(12) United States Patent
Zucherman et al.

(10) Patent No.: US 7,497,859 B2
(45) Date of Patent: Mar. 3, 2009

(54) TOOLS FOR IMPLANTING AN ARTIFICIAL VERTEBRAL DISK

(75) Inventors: James F. Zucherman, San Francisco, CA (US); Ken Y. Hsu, San Francisco, CA (US); Charles J. Winslow, Walnut Creek, CA (US); Scott A. Yerby, Montara, CA (US); Steve Mitchell, Pleasant Hill, CA (US); John Flynn, Concord, CA (US)

(73) Assignee: Kyphon SARL (CH)

( * ) Notice: Subject to any disclaimer, the term of this patent is extended or adjusted under 35 U.S.C. 154(b) by 0 days.

(21) Appl. No.: 10/685,134

(22) Filed: Oct. 14, 2003

(65) Prior Publication Data

US 2004/0143270 A1   Jul. 22, 2004

Related U.S. Application Data

(60) Provisional application No. 60/422,011, filed on Oct. 29, 2002.

(51) Int. Cl.
*A61B 17/00* (2006.01)

(52) U.S. Cl. ............... 606/79; 30/304; 30/167; D8/47

(58) Field of Classification Search ............. 606/79, 606/61, 80, 167, 170, 172, 99, 90, 105; 623/17.11–17.16; 600/201, 210, 214; D8/47, 20; 30/167, 167.1, 30/167.2, 304, 299
See application file for complete search history.

(56) References Cited

U.S. PATENT DOCUMENTS

| | | | | |
|---|---|---|---|---|
| 482,704 | A | * | 9/1892 | Wall ............... 30/167.1 |
| 1,086,266 | A | * | 2/1914 | Bell ............... 452/147 |
| 2,322,503 | A | * | 6/1943 | Bowman ............... 30/148 |
| 2,397,875 | A | * | 4/1946 | Marshaus ............... 30/304 |
| 2,456,806 | A | | 12/1948 | Wolffe |
| 2,539,849 | A | * | 1/1951 | Lum ............... 294/61 |
| 2,677,369 | A | | 5/1954 | Knowles ............... 128/92 |

(Continued)

FOREIGN PATENT DOCUMENTS

CA   2015507   1/1991

(Continued)

OTHER PUBLICATIONS

Ceramic Interspinous Block (CISB) Assisted Anterior Interbody Fusion, Haruo Tsuji, Norikazu Hirano, Yoshiharu Katoh, Hiroshi Ohsima, Hirokazu Ishihara, Hisao Matsui, and Yohihiko Hayashi, *Journal of Spinal Disorders* vol. 3. No. 1, pp. 77-86, c1990 Raven Press, Ltd., New York.

(Continued)

*Primary Examiner*—Eduardo C Robert
*Assistant Examiner*—Mary Hoffman
(74) *Attorney, Agent, or Firm*—Haynes and Boone, LLP

(57) ABSTRACT

This invention relates to tools for preparing vertebral bodies in the spine for the implantation of an artificial vertebral disk replacement and related method. A first tool is disclosed that prepares the vertebral bodies for implantation by cutting offset channels in the vertebral bodies. The second tool holds two plates of the implant during the implantation process. This invention also relates to an artificial vertebral disk replacement, a method of operation, and a method of implanting.

12 Claims, 22 Drawing Sheets

U.S. PATENT DOCUMENTS

| | | |
|---|---|---|
| 3,426,364 A | 2/1969 | Lumb |
| 3,648,691 A | 3/1972 | Lumb ................... 128/92 |
| 3,867,728 A | 2/1975 | Stubstad et al. |
| 3,875,595 A | 4/1975 | Froning |
| 4,309,777 A | 1/1982 | Patil |
| 4,349,921 A | 9/1982 | Kuntz |
| 4,369,769 A | 1/1983 | Edwards |
| 4,401,112 A | 8/1983 | Rezaian |
| 4,479,491 A | 10/1984 | Martin |
| 4,501,269 A | 2/1985 | Bagby |
| 4,553,273 A | 11/1985 | Wu |
| 4,554,914 A | 11/1985 | Kapp et al. |
| 4,599,084 A | 7/1986 | Nashef |
| 4,599,086 A | 7/1986 | Doty |
| 4,636,217 A | 1/1987 | Ogilvie |
| 4,657,550 A | 4/1987 | Daher |
| 4,685,447 A | 8/1987 | Iversen et al. |
| 4,696,290 A | 9/1987 | Steffee |
| 4,714,469 A | 12/1987 | Kenna |
| 4,743,256 A | 5/1988 | Brantigan |
| 4,759,766 A | 7/1988 | Buttner-Janz et al. |
| 4,759,769 A | 7/1988 | Hedman et al. |
| 4,772,287 A | 9/1988 | Ray et al. |
| 4,790,303 A | 12/1988 | Steffee |
| 4,834,757 A | 5/1989 | Brantigan |
| 4,863,477 A | 9/1989 | Monson |
| 4,874,389 A | 10/1989 | Downey |
| 4,878,915 A | 11/1989 | Brantigan |
| 4,904,260 A | 2/1990 | Ray et al. |
| 4,904,261 A | 2/1990 | Dove et al. |
| 4,911,718 A | 3/1990 | Lee et al. |
| 4,932,969 A | 6/1990 | Frey et al. |
| 4,932,975 A | 6/1990 | Main et al. |
| 4,936,848 A | 6/1990 | Bagby |
| 4,946,378 A | 8/1990 | Hirayama et al. |
| 4,961,740 A | 10/1990 | Ray et al. |
| 4,969,888 A | 11/1990 | Scholten et al. |
| 4,997,432 A | 3/1991 | Keller |
| 5,002,576 A | 3/1991 | Furhmann et al. |
| 5,011,484 A | 4/1991 | Breard ................... 606/61 |
| 5,015,247 A | 5/1991 | Michelson |
| 5,026,373 A | 6/1991 | Ray et al. |
| 5,035,716 A | 7/1991 | Downey |
| 5,047,055 A | 9/1991 | Bao et al. |
| 5,052,373 A * | 10/1991 | Michelson ................... 600/217 |
| 5,055,104 A | 10/1991 | Ray |
| 5,059,193 A | 10/1991 | Kuslich |
| 5,059,194 A | 10/1991 | Michelson |
| 5,071,437 A | 12/1991 | Steffee |
| 5,108,438 A | 4/1992 | Stone |
| 5,108,442 A | 4/1992 | Smith |
| 5,122,130 A | 6/1992 | Keller |
| 5,123,926 A | 6/1992 | Pisharodi |
| 5,167,662 A | 12/1992 | Hayes et al. |
| 5,171,280 A | 12/1992 | Baumgartner |
| 5,171,281 A | 12/1992 | Parsons et al. |
| 5,180,381 A | 1/1993 | Aust et al. |
| 5,192,326 A | 3/1993 | Bao et al. |
| 5,192,327 A | 3/1993 | Brantigan |
| 5,246,458 A | 9/1993 | Graham |
| 5,258,031 A | 11/1993 | Salib et al. |
| 5,258,043 A | 11/1993 | Stone |
| 5,263,953 A | 11/1993 | Bagby |
| 5,290,312 A | 3/1994 | Kojimoto et al. |
| 5,306,307 A | 4/1994 | Senter |
| 5,306,308 A | 4/1994 | Gross et al. |
| 5,306,309 A | 4/1994 | Wagner et al. |
| 5,313,962 A | 5/1994 | Obenchain |
| 5,314,477 A | 5/1994 | Marnay |
| 5,314,478 A | 5/1994 | Oka et al. |
| 5,320,644 A | 6/1994 | Baumgartner |
| 5,336,223 A | 8/1994 | Rogers |
| 5,350,397 A | 9/1994 | Palermo et al. |
| 5,352,225 A | 10/1994 | Yuan et al. |
| 5,354,302 A | 10/1994 | Ko |
| 5,360,430 A | 11/1994 | Lin |
| 5,366,508 A | 11/1994 | Brekke |
| 5,370,693 A | 12/1994 | Kelman et al. |
| 5,370,697 A | 12/1994 | Baumgartner |
| 5,375,823 A | 12/1994 | Navas |
| 5,383,884 A | 1/1995 | Summers |
| 5,390,683 A | 2/1995 | Pisharodi |
| 5,395,317 A | 3/1995 | Kambin |
| 5,395,372 A | 3/1995 | Holt et al. |
| 5,397,364 A | 3/1995 | Kozak et al. |
| 5,401,269 A | 3/1995 | Buttner-Janz et al. |
| 5,415,704 A | 5/1995 | Davidson |
| 5,423,816 A | 6/1995 | Lin |
| 5,423,817 A | 6/1995 | Lin |
| 5,423,825 A * | 6/1995 | Levine ................... 606/86 |
| 5,425,772 A | 6/1995 | Brantigan |
| 5,425,773 A | 6/1995 | Boyd et al. |
| 5,425,777 A | 6/1995 | Sarkisian et al. |
| 5,431,658 A | 7/1995 | Moskovich |
| 5,439,464 A | 8/1995 | Shapiro |
| 5,443,514 A | 8/1995 | Steffee |
| 5,443,515 A | 8/1995 | Cohen et al. |
| 5,445,639 A | 8/1995 | Kuslich et al. |
| 5,454,812 A | 10/1995 | Lin |
| 5,456,722 A | 10/1995 | McLeod et al. |
| 5,458,638 A | 10/1995 | Kuslich et al. |
| 5,458,641 A | 10/1995 | Ramirez Jimenez |
| 5,458,642 A | 10/1995 | Beer et al. |
| 5,458,643 A | 10/1995 | Oka et al. |
| 5,480,401 A | 1/1996 | Navas |
| 5,480,442 A | 1/1996 | Bertagnoli |
| 5,484,437 A | 1/1996 | Michelson |
| 5,489,307 A | 2/1996 | Kuslich et al. |
| 5,489,308 A | 2/1996 | Kuslich et al. |
| 5,496,318 A | 3/1996 | Howland ................... 606/61 |
| 5,505,732 A | 4/1996 | Michelson |
| 5,507,816 A | 4/1996 | Bullivant |
| 5,514,180 A | 5/1996 | Heggeness et al. |
| 5,522,899 A | 6/1996 | Michelson |
| 5,527,312 A | 6/1996 | Ray |
| 5,531,793 A | 7/1996 | Kelman et al. |
| 5,534,023 A | 7/1996 | Henley |
| 5,534,028 A | 7/1996 | Bao et al. |
| 5,534,029 A | 7/1996 | Shima |
| 5,534,030 A | 7/1996 | Navarro et al. |
| 5,534,031 A | 7/1996 | Matsuzaki et al. |
| 5,540,689 A | 7/1996 | Sanders et al. |
| 5,545,229 A | 8/1996 | Parsons et al. |
| 5,549,679 A | 8/1996 | Kuslich |
| 5,554,191 A | 9/1996 | Lahille et al. |
| 5,556,431 A | 9/1996 | Buttner-Janz |
| 5,562,736 A | 10/1996 | Ray et al. |
| 5,562,738 A | 10/1996 | Boyd et al. |
| 5,571,109 A | 11/1996 | Bertagnoli |
| 5,571,189 A | 11/1996 | Kuslich |
| 5,571,190 A | 11/1996 | Ulrich et al. |
| 5,571,192 A | 11/1996 | Schönhöffer |
| 5,591,235 A | 1/1997 | Kuslich |
| 5,593,409 A | 1/1997 | Michelson |
| 5,599,279 A | 2/1997 | Slotman et al. |
| 5,601,556 A | 2/1997 | Pisharodi |
| 5,603,713 A | 2/1997 | Aust et al. |
| 5,609,634 A | 3/1997 | Voydeville ................... 623/17 |
| 5,609,635 A | 3/1997 | Michelson |
| 5,609,636 A | 3/1997 | Kohrs et al. |
| 5,620,458 A | 4/1997 | Green et al. |
| 5,645,592 A | 7/1997 | Nicolais et al. |
| 5,645,596 A | 7/1997 | Kim et al. |
| 5,645,597 A | 7/1997 | Krapiva |

| Patent | Date | Inventor |
|---|---|---|
| 5,645,598 A | 7/1997 | Brosnahan, III |
| 5,645,599 A | 7/1997 | Samani |
| 5,653,761 A | 8/1997 | Pisharodi |
| 5,653,762 A | 8/1997 | Pisharodi |
| 5,658,335 A | 8/1997 | Allen |
| 5,658,336 A | 8/1997 | Pisharodi |
| 5,658,337 A | 8/1997 | Kohrs et al. |
| 5,669,909 A | 9/1997 | Zdeblick et al. |
| 5,674,294 A | 10/1997 | Bainville et al. |
| 5,674,295 A | 10/1997 | Ray et al. |
| 5,674,296 A | 10/1997 | Bryan et al. |
| 5,676,701 A | 10/1997 | Yuan et al. |
| 5,676,702 A | 10/1997 | Ratron |
| 5,683,463 A | 11/1997 | Godefroy et al. |
| 5,683,464 A | 11/1997 | Wagner et al. |
| 5,683,465 A | 11/1997 | Shinn et al. |
| 5,693,100 A | 12/1997 | Pisharodi |
| 5,697,889 A | 12/1997 | Slotman et al. |
| 5,697,977 A | 12/1997 | Pisharodi |
| 5,700,292 A | 12/1997 | Margulies |
| 5,702,449 A | 12/1997 | McKay |
| 5,702,450 A | 12/1997 | Bisserie |
| 5,702,454 A | 12/1997 | Baumgartner |
| 5,702,455 A | 12/1997 | Saggar |
| 5,716,415 A | 2/1998 | Steffee |
| 5,716,416 A | 2/1998 | Lin |
| 5,741,253 A | 4/1998 | Michelson |
| 5,755,732 A | 5/1998 | Green et al. |
| 5,755,796 A | 5/1998 | Ibo et al. |
| 5,755,798 A | 5/1998 | Papavero et al. |
| 5,766,252 A | 6/1998 | Henry et al. |
| 5,772,661 A | 6/1998 | Michelson |
| 5,776,196 A | 7/1998 | Matsuzaki et al. |
| 5,776,199 A | 7/1998 | Michelson |
| 5,782,830 A | 7/1998 | Farris |
| 5,782,832 A | 7/1998 | Larsen et al. |
| 5,782,919 A | 7/1998 | Zdeblick et al. |
| 5,797,909 A | 8/1998 | Michelson |
| 5,800,438 A | 9/1998 | Tuke et al. |
| 5,800,550 A | 9/1998 | Sertich |
| 5,824,093 A | 10/1998 | Ray et al. |
| 5,824,094 A | 10/1998 | Serhan et al. |
| 5,827,328 A | 10/1998 | Buttermann |
| 5,836,948 A | 11/1998 | Zucherman et al. |
| 5,860,973 A | 1/1999 | Michelson |
| 5,860,977 A | 1/1999 | Zucherman et al. |
| 5,865,845 A | 2/1999 | Thalgott |
| 5,865,846 A | 2/1999 | Bryan et al. |
| 5,876,404 A | 3/1999 | Zucherman et al. |
| 5,885,292 A | 3/1999 | Moskovitz et al. |
| 5,885,299 A | 3/1999 | Winslow et al. |
| 5,888,222 A | 3/1999 | Coates et al. |
| 5,888,224 A | 3/1999 | Beckers et al. |
| 5,888,226 A | 3/1999 | Rogozinski |
| 5,888,227 A | 3/1999 | Cottle |
| 5,891,147 A | 4/1999 | Moskovitz et al. |
| 5,893,889 A | 4/1999 | Harrington |
| 5,893,890 A | 4/1999 | Pisharodi |
| 5,895,426 A | 4/1999 | Scarborough et al. |
| 5,895,427 A | 4/1999 | Kuslich et al. |
| 5,895,428 A | 4/1999 | Berry |
| 5,899,941 A | 5/1999 | Nishijima et al. |
| 5,906,616 A | 5/1999 | Pavlov et al. |
| 5,919,235 A | 7/1999 | Husson et al. |
| 5,928,284 A | 7/1999 | Mehdizadeh |
| 5,944,754 A | 8/1999 | Vacanti |
| 5,945,115 A | 8/1999 | Dunn et al. |
| 5,961,554 A | 10/1999 | Jamson et al. |
| 5,964,807 A | 10/1999 | Gan et al. |
| 5,976,186 A | 11/1999 | Bao et al. |
| 5,980,572 A | 11/1999 | Kim et al. |
| 5,984,967 A | 11/1999 | Zdeblick et al. |
| 5,989,291 A | 11/1999 | Ralph et al. |
| 6,001,130 A | 12/1999 | Bryan et al. |
| 6,004,573 A | 12/1999 | Rathi et al. |
| 6,005,162 A | 12/1999 | Constantz |
| 6,019,792 A | 2/2000 | Cauthen |
| 6,019,793 A | 2/2000 | Perren et al. |
| 6,022,376 A | 2/2000 | Assell et al. |
| 6,039,761 A | 3/2000 | Li et al. |
| 6,039,763 A | 3/2000 | Shelokov |
| 6,042,582 A | 3/2000 | Ray |
| 6,045,579 A | 4/2000 | Hochshuler et al. |
| 6,045,580 A | 4/2000 | Scarborough et al. |
| 6,048,342 A | 4/2000 | Zucherman |
| 6,051,648 A | 4/2000 | Rhee et al. |
| 6,068,630 A | 5/2000 | Zucherman |
| 6,074,390 A | 6/2000 | Zucherman et al. |
| 6,080,155 A | 6/2000 | Michelson |
| 6,080,158 A | 6/2000 | Lin |
| 6,080,193 A | 6/2000 | Hochshuler et al. |
| 6,086,613 A | 7/2000 | Camino et al. |
| 6,090,112 A | 7/2000 | Zucherman et al. |
| 6,093,205 A | 7/2000 | McLeod et al. |
| 6,096,038 A | 8/2000 | Michelson |
| 6,096,080 A | 8/2000 | Nicholson et al. |
| 6,099,531 A | 8/2000 | Bonutti |
| 6,102,950 A | 8/2000 | Vaccaro |
| 6,110,210 A | 8/2000 | Norton et al. |
| 6,111,164 A | 8/2000 | Rainey et al. |
| 6,113,602 A * | 9/2000 | Sand ........................ 606/61 |
| 6,113,637 A | 9/2000 | Gill et al. |
| 6,113,638 A | 9/2000 | Williams et al. |
| 6,113,639 A | 9/2000 | Ray et al. |
| 6,120,502 A | 9/2000 | Michelson |
| 6,120,503 A | 9/2000 | Michelson |
| 6,123,705 A | 9/2000 | Michelson |
| 6,126,689 A | 10/2000 | Brett |
| 6,127,597 A | 10/2000 | Beyar et al. |
| 6,129,763 A | 10/2000 | Chauvin et al. |
| 6,132,430 A | 10/2000 | Wagner |
| 6,132,465 A | 10/2000 | Ray et al. |
| 6,136,001 A | 10/2000 | Michelson |
| 6,136,031 A | 10/2000 | Middleton |
| 6,139,579 A | 10/2000 | Steffee et al. |
| 6,146,421 A | 11/2000 | Gordon et al. |
| 6,146,422 A | 11/2000 | Lawson |
| 6,149,650 A | 11/2000 | Michelson |
| 6,149,652 A | 11/2000 | Zucherman et al. |
| 6,149,686 A | 11/2000 | Kuslich et al. |
| 6,152,926 A | 11/2000 | Zucherman et al. |
| 6,156,038 A | 12/2000 | Zucherman et al. |
| 6,156,067 A | 12/2000 | Bryan et al. |
| 6,159,215 A | 12/2000 | Urbahns et al. |
| 6,162,252 A | 12/2000 | Kuras et al. |
| 6,165,218 A | 12/2000 | Husson et al. |
| 6,176,882 B1 | 1/2001 | Biedermann et al. |
| 6,179,874 B1 | 1/2001 | Cauthen |
| 6,183,471 B1 | 2/2001 | Zucherman et al. |
| 6,190,387 B1 | 2/2001 | Zucherman et al. |
| 6,190,414 B1 | 2/2001 | Young et al. |
| 6,193,757 B1 | 2/2001 | Foley et al. |
| 6,197,033 B1 * | 3/2001 | Haid et al. .................... 606/99 |
| 6,206,922 B1 | 3/2001 | Zdeblick et al. |
| 6,210,412 B1 | 4/2001 | Michelson |
| 6,224,595 B1 | 5/2001 | Michelson |
| 6,224,607 B1 | 5/2001 | Michelson |
| 6,224,631 B1 | 5/2001 | Kohrs |
| 6,228,118 B1 | 5/2001 | Gordon |
| 6,231,609 B1 | 5/2001 | Mehdizadeh |
| 6,234,705 B1 | 5/2001 | Troxell |
| 6,235,030 B1 | 5/2001 | Zucherman et al. |
| 6,238,397 B1 | 5/2001 | Zucherman et al. |
| 6,241,769 B1 | 6/2001 | Nicholson et al. |
| 6,241,770 B1 | 6/2001 | Michelson |
| 6,241,771 B1 | 6/2001 | Gresser et al. |

| | | | | | | |
|---|---|---|---|---|---|---|
| 6,245,072 B1 | 6/2001 | Zdeblick et al. | | 6,478,822 B1 | 11/2002 | Leroux et al. |
| 6,245,108 B1 | 6/2001 | Biscup | | 6,478,823 B1 | 11/2002 | Michelson |
| 6,258,125 B1 | 7/2001 | Paul et al. | | 6,482,233 B1 | 11/2002 | Aebi et al. |
| 6,261,296 B1 | 7/2001 | Aebi et al. | | 6,482,235 B1 | 11/2002 | Lambrecht et al. |
| 6,264,655 B1 | 7/2001 | Pisharodi | | 6,485,517 B1 | 11/2002 | Michelson |
| 6,264,656 B1 | 7/2001 | Michelson | | 6,488,710 B2 | 12/2002 | Besselink |
| 6,264,695 B1 | 7/2001 | Stoy | | 6,500,178 B2 | 12/2002 | Zucherman et al. |
| 6,270,498 B1 | 8/2001 | Michelson | | 6,500,205 B1 | 12/2002 | Michelson |
| 6,277,149 B1 | 8/2001 | Boyle et al. | | 6,503,279 B1 | 1/2003 | Webb et al. |
| 6,280,444 B1 | 8/2001 | Zucherman et al. | | 6,514,256 B2 | 2/2003 | Zucherman et al. |
| 6,280,475 B1 | 8/2001 | Bao et al. | | 6,517,580 B1 | 2/2003 | Ramadan et al. |
| 6,287,343 B1 | 9/2001 | Kuslich et al. | | 6,520,993 B2 | 2/2003 | James et al. |
| 6,296,664 B1 | 10/2001 | Middleton | | 6,520,996 B1 | 2/2003 | Manasas et al. |
| 6,296,665 B1 | 10/2001 | Strnad et al. | | 6,524,312 B2 | 2/2003 | Landry et al. |
| 6,302,914 B1 | 10/2001 | Michelson | | 6,527,773 B1 | 3/2003 | Lin et al. |
| 6,309,421 B1 | 10/2001 | Pisharodi | | 6,527,804 B1 | 3/2003 | Gauchet et al. |
| 6,311,562 B1 | 11/2001 | Hanada | | 6,527,806 B2 | 3/2003 | Ralph et al. |
| 6,315,795 B1 | 11/2001 | Scarborough et al. | | 6,530,933 B1 | 3/2003 | Yeung et al. |
| 6,315,797 B1 | 11/2001 | Middleton | | 6,530,955 B2 | 3/2003 | Boyle et al. |
| 6,325,827 B1 | 12/2001 | Lin | | 6,540,785 B1 | 4/2003 | Gill et al. |
| 6,332,882 B1 | 12/2001 | Zucherman et al. | | 6,547,823 B2 | 4/2003 | Scarborough et al. |
| 6,332,883 B1 | 12/2001 | Zucherman et al. | | 6,548,002 B2 | 4/2003 | Gresser et al. |
| 6,342,074 B1 | 1/2002 | Simpson | | 6,554,863 B2 | 4/2003 | Paul et al. |
| 6,348,071 B1 | 2/2002 | Steffee et al. | | 6,558,386 B1 | 5/2003 | Cragg |
| 6,350,283 B1 | 2/2002 | Michelson | | 6,558,387 B2 | 5/2003 | Errico et al. |
| 6,364,880 B1 | 4/2002 | Michelson | | 6,558,390 B2 | 5/2003 | Cragg |
| 6,368,350 B1 | 4/2002 | Erickson et al. | | 6,558,423 B1 | 5/2003 | Michelson |
| 6,368,351 B1 | 4/2002 | Glenn et al. | | 6,558,424 B2 | 5/2003 | Thalgott |
| 6,371,984 B1 | 4/2002 | Van Dyke et al. | | 6,562,073 B2 | 5/2003 | Foley |
| 6,371,988 B1 | 4/2002 | Pafford et al. | | 6,562,074 B2 | 5/2003 | Gerbec et al. |
| 6,371,989 B1 | 4/2002 | Chauvin et al. | | 6,565,570 B2 | 5/2003 | Sterett et al. |
| 6,379,355 B1 | 4/2002 | Zucherman et al. | | 6,569,201 B2 | 5/2003 | Moumene et al. |
| 6,379,385 B1 | 4/2002 | Kalas et al. | | 6,572,653 B1 | 6/2003 | Simonson |
| 6,383,221 B1 | 5/2002 | Scarborough et al. | | 6,572,654 B1 | 6/2003 | Santilli |
| 6,391,030 B1 | 5/2002 | Wagner et al. | | 6,575,982 B1 | 6/2003 | Bonutti |
| 6,391,058 B1 | 5/2002 | Kuslich et al. | | 6,576,016 B1 | 6/2003 | Hochshuler et al. |
| 6,395,030 B1 | 5/2002 | Songer et al. | | 6,576,017 B2 | 6/2003 | Foley et al. |
| 6,395,031 B1 | 5/2002 | Foley et al. | | 6,579,318 B2 | 6/2003 | Varga et al. |
| 6,395,032 B1 | 5/2002 | Gauchet | | 6,579,320 B1 | 6/2003 | Gauchet et al. |
| 6,395,034 B1 | 5/2002 | Suddaby | | 6,579,321 B1 | 6/2003 | Gordon et al. |
| 6,402,785 B1 | 6/2002 | Zdeblick et al. | | 6,582,432 B1 | 6/2003 | Michelson |
| 6,409,766 B1 | 6/2002 | Brett | | 6,582,437 B2 * | 6/2003 | Dorchak et al. ............... 606/90 |
| 6,413,278 B1 | 7/2002 | Marchosky | | 6,582,468 B1 | 6/2003 | Gauchet |
| 6,416,551 B1 | 7/2002 | Keller | | 6,626,944 B1 | 9/2003 | Taylor |
| 6,419,676 B1 | 7/2002 | Zucherman et al. | | 6,641,582 B1 * | 11/2003 | Hanson et al. ............... 606/61 |
| 6,419,677 B2 | 7/2002 | Zucherman et al. | | 6,682,562 B2 | 1/2004 | Viart et al. |
| 6,419,704 B1 | 7/2002 | Ferree | | 6,699,246 B2 | 3/2004 | Zucherman et al. |
| 6,419,706 B1 | 7/2002 | Graf | | 6,706,068 B2 | 3/2004 | Ferree |
| 6,423,063 B1 | 7/2002 | Bonutti | | 6,706,070 B1 | 3/2004 | Wagner et al. |
| 6,423,095 B1 | 7/2002 | Van Hoech et al. | | 6,712,825 B2 * | 3/2004 | Aebi et al. ................. 606/90 |
| 6,425,920 B1 | 7/2002 | Hamada | | 6,740,118 B2 | 5/2004 | Eisermann et al. |
| 6,432,106 B1 | 8/2002 | Fraser | | 6,755,841 B2 * | 6/2004 | Fraser et al. ................. 606/99 |
| 6,436,098 B1 | 8/2002 | Michelson | | 6,770,095 B2 | 8/2004 | Grinberg et al. .......... 623/17.14 |
| 6,436,119 B1 | 8/2002 | Erb et al. | | 2001/0012938 A1 | 8/2001 | Zucherman et al. |
| 6,436,140 B1 | 8/2002 | Liu et al. | | 2002/0010473 A1 * | 1/2002 | Lin ............... 606/99 |
| 6,436,142 B1 | 8/2002 | Paes et al. | | 2002/0128715 A1 | 9/2002 | Bryan et al. |
| 6,440,168 B1 | 8/2002 | Cauthen | | 2003/0149438 A1 * | 8/2003 | Nichols et al. .............. 606/99 |
| 6,440,169 B1 | 8/2002 | Elberg et al. | | 2003/0208273 A1 | 11/2003 | Eisermann et al. |
| 6,443,990 B1 | 9/2002 | Aebi et al. | | 2004/0002758 A1 * | 1/2004 | Landry et al. ............ 623/17.11 |
| 6,447,512 B1 | 9/2002 | Landry et al. | | 2004/0073313 A1 | 4/2004 | Link et al. |
| 6,447,544 B1 | 9/2002 | Michelson | | 2004/0106998 A1 | 6/2004 | Ferree |
| 6,447,547 B1 | 9/2002 | Michelson | | 2004/0117022 A1 | 6/2004 | Marnay et al. |
| 6,451,019 B1 | 9/2002 | Zucherman et al. | | 2004/0138750 A1 | 7/2004 | Mitchell |
| 6,451,020 B1 | 9/2002 | Zucherman et al. | | 2004/0143332 A1 | 7/2004 | Krueger et al. |
| 6,454,804 B1 | 9/2002 | Ferree | | 2004/0225295 A1 * | 11/2004 | Zubok et al. .............. 606/90 |
| 6,454,807 B1 | 9/2002 | Jackson | | 2004/0225360 A1 | 11/2004 | Malone |
| 6,458,131 B1 | 10/2002 | Ray | | 2004/0225365 A1 | 11/2004 | Eisermann et al. |
| 6,458,159 B1 | 10/2002 | Thalgott | | 2004/0225366 A1 | 11/2004 | Eisermann et al. |
| 6,461,359 B1 | 10/2002 | Tribus et al. | | 2005/0113842 A1 * | 5/2005 | Bertagnoli et al. ............ 606/90 |
| 6,468,310 B1 | 10/2002 | Ralph et al. | | | | |
| 6,471,724 B2 | 10/2002 | Zdeblick et al. | | | FOREIGN PATENT DOCUMENTS | |
| 6,475,219 B1 | 11/2002 | Shelokov | | | | |
| 6,478,796 B2 | 11/2002 | Zucherman et al. | | DE | 3113142 | 1/1982 |

| | | |
|---|---|---|
| DE | 4012622 | 7/1991 |
| EP | 0307241 B1 | 3/1989 |
| EP | 0322334 | 6/1989 |
| FR | 2722980 | 7/1994 |
| FR | 2705227 | 11/1994 |
| FR | 2707864 | 1/1995 |
| FR | 2717066 | 9/1995 |
| FR | 2717068 | 9/1995 |
| FR | 2722088 | 1/1996 |
| FR | 2724554 | 3/1996 |
| FR | 2730156 A1 | 8/1996 |
| FR | 2780269 A1 | 12/1999 |
| FR | 2806614 A1 | 9/2001 |
| GB | 780652 | 8/1957 |
| WO | WO 90/00037 | 1/1990 |
| WO | WO 95/31158 A | 11/1995 |
| WO | WO 99/26562 | 6/1999 |
| WO | WO 99/59669 | 11/1999 |
| WO | WO 00/04851 | 2/2000 |
| WO | WO 00/13619 | 3/2000 |
| WO | WO 00/13620 | 3/2000 |
| WO | WO 00/23015 A1 | 4/2000 |
| WO | 01/01893 A1 | 1/2001 |
| WO | WO 01/89428 A2 | 11/2001 |

OTHER PUBLICATIONS

*Instrumentation and Implants for Spinal Surgery*, J. Dabb, *Diary of the XVIIIth Scientific Meeting of the PTO Tr/Pamietnik XVIII Zjazdu Naukowego PTOTr/PZ,WL, Warszawa*, Link America Inc., 1971, 665.

*Spinal Stenosis and Neurogenic Claudication*, Richard W. Porter, MD, FRCS, FRCSE, *Spine* vol. 21, No. 17, pp. 2046-2052, c1996, Lippincott-Raven Publishers.

*Preliminary Design and Experimental Studies of a Novel Soft Implant for Correcting Sagittal Plan Instability in the Lumbar Spine*, R.J.Minns, BEng, Msc, PhD, DscTech, and W.K. Walsh, FRCS, *Spine* vol. 22, No. 16, pp. 1819-1827, c1997, Lippincott-Raven Publishers.

International Search Report for PCT/US06/10521 (mailed Nov. 22, 2006).

* cited by examiner

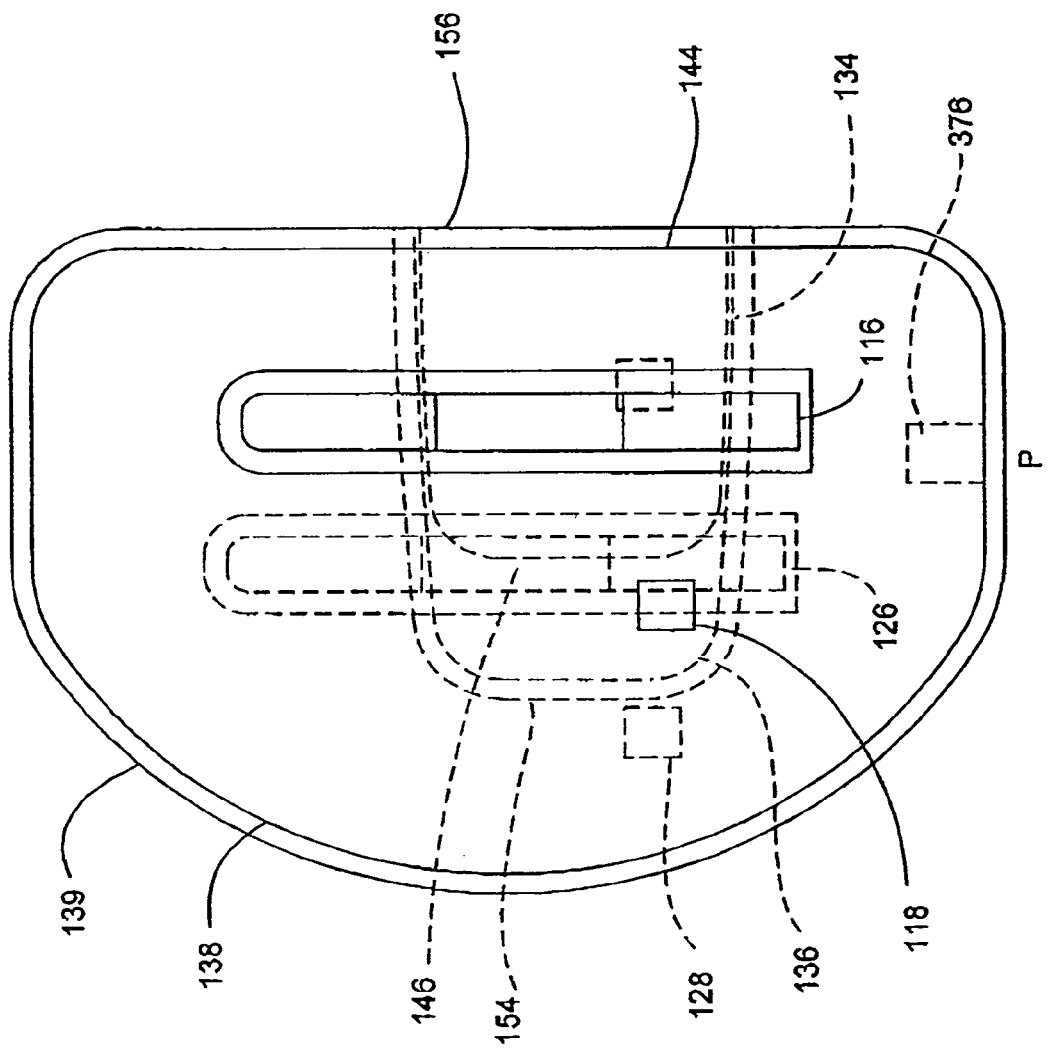

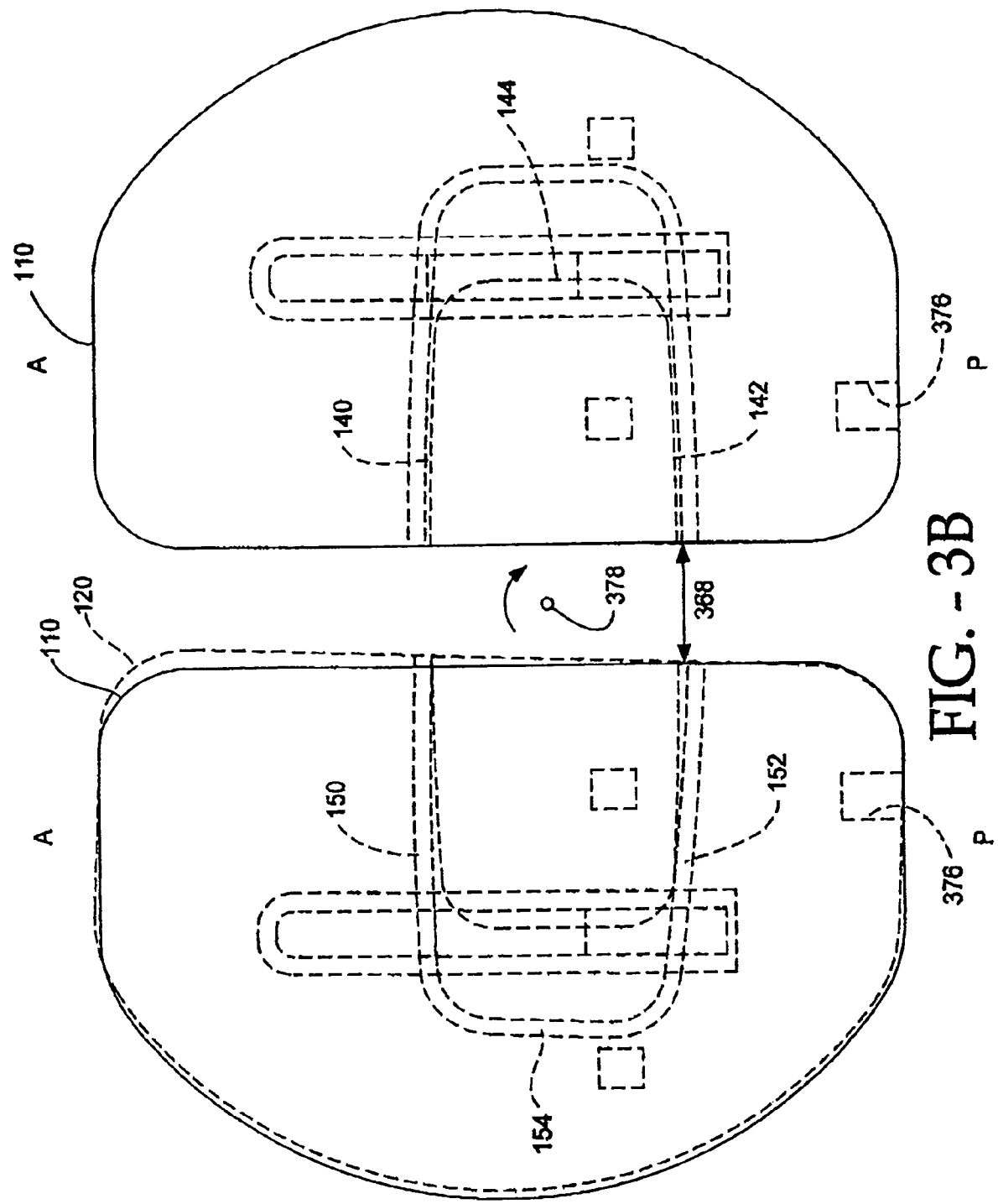

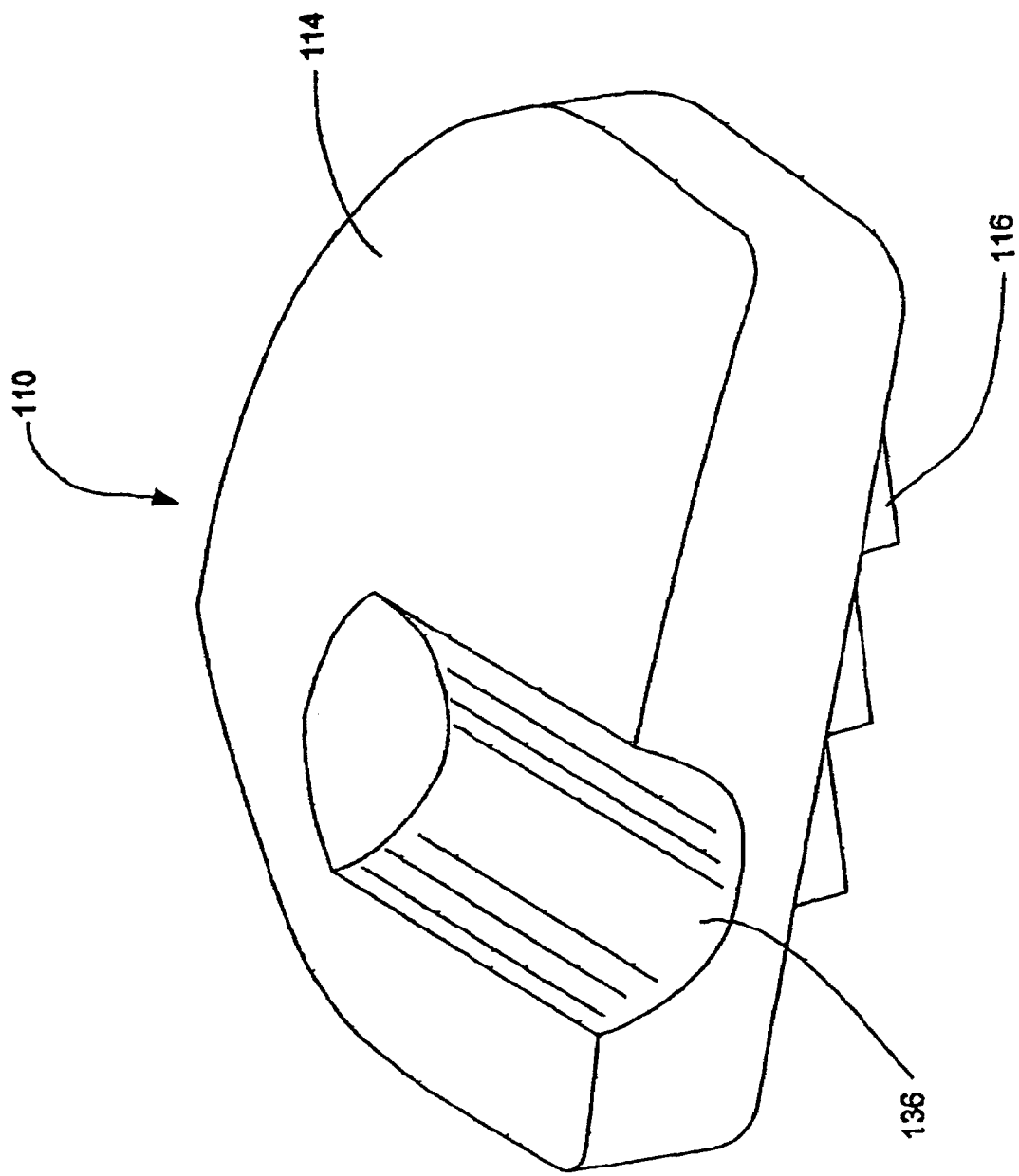

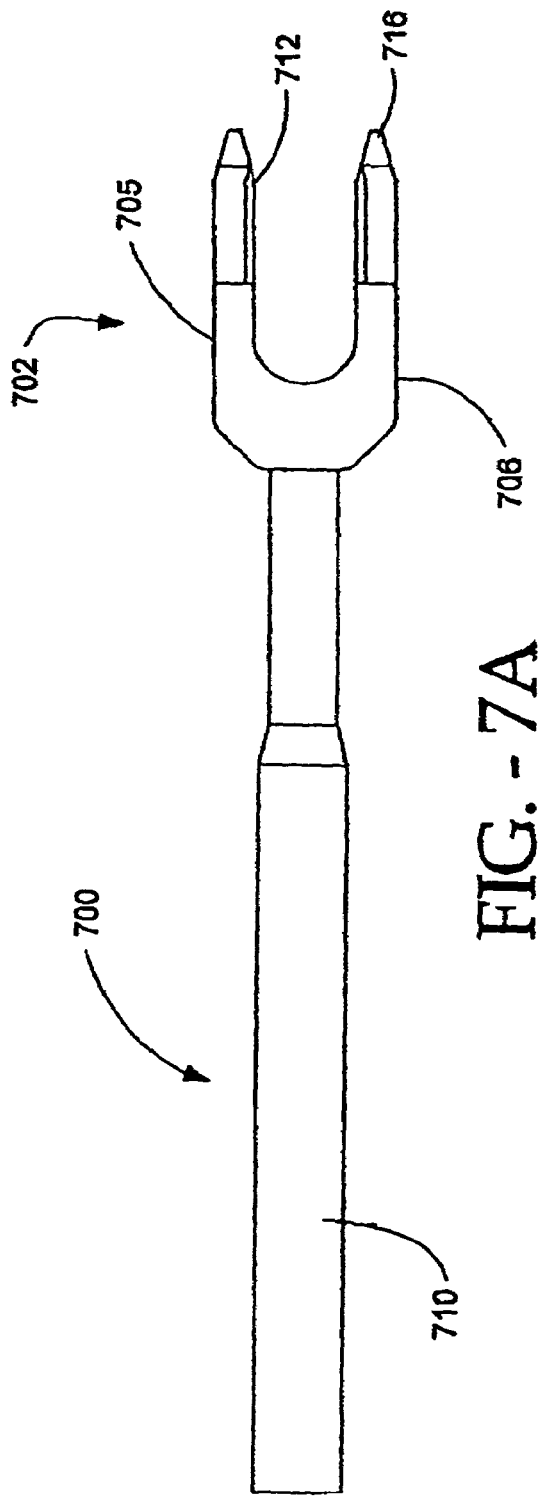
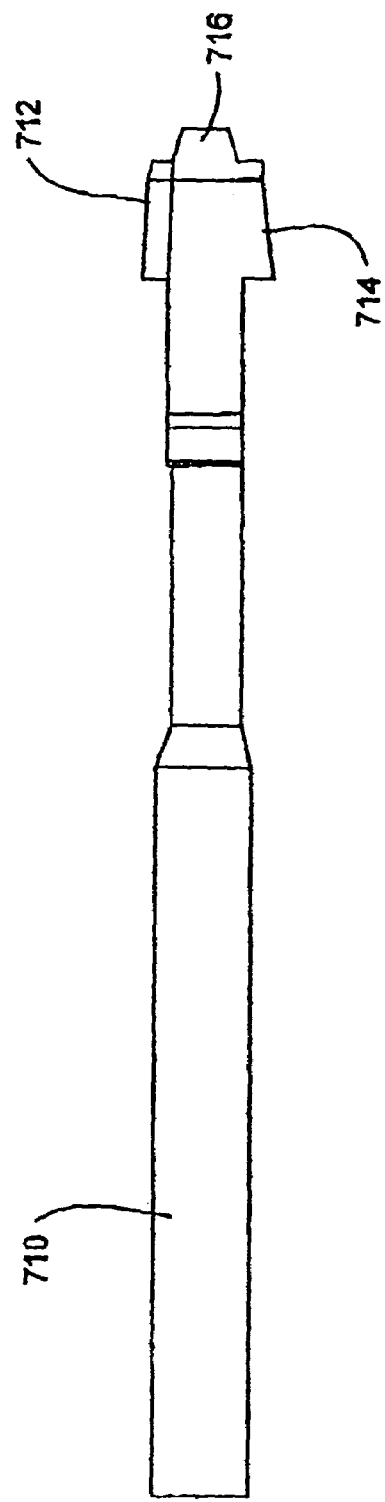
FIG. - 7A
FIG. - 7B

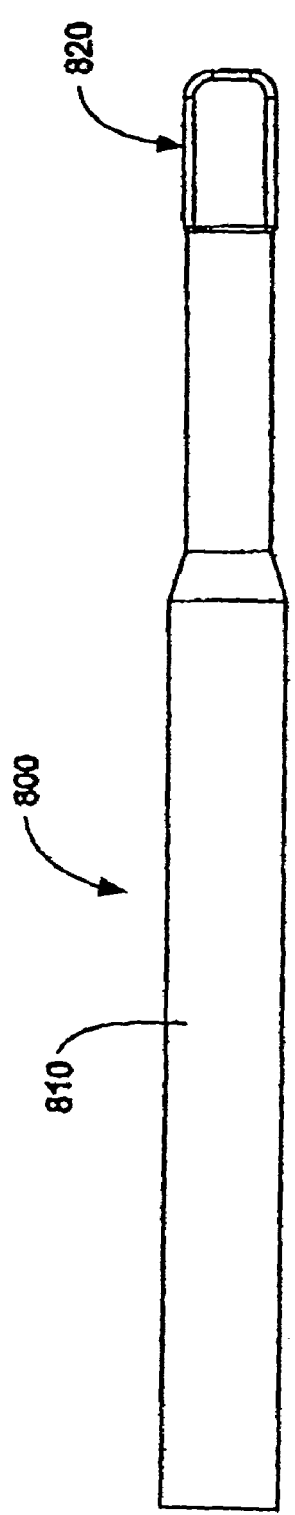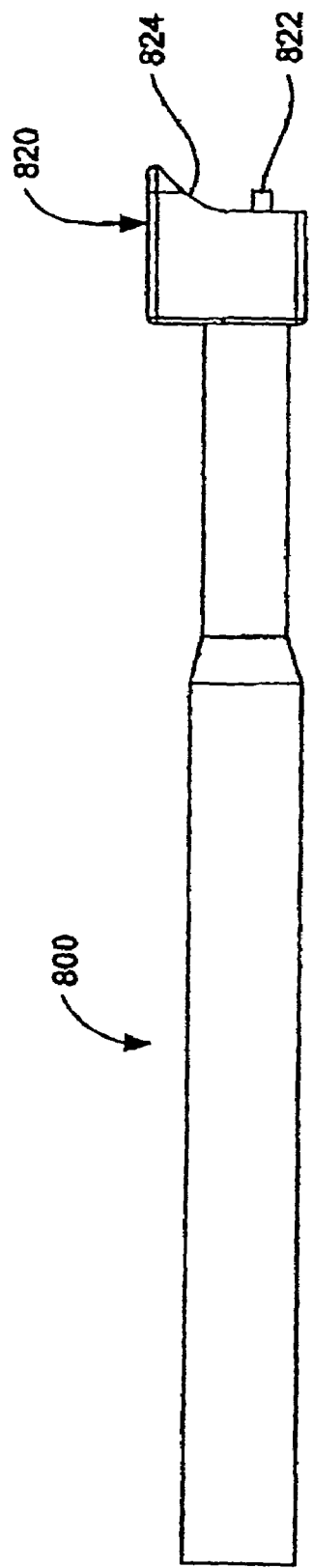
FIG. - 8A
FIG. - 8B

TOOLS FOR IMPLANTING AN ARTIFICIAL VERTEBRAL DISK

CLAIM OF PRIORITY

This application claims priority to U.S. Provisional Application No. 60/422,011, filed on Oct. 29, 2002, entitled "TOOLS FOR IMPLANTING AN ARTIFICIAL VERTEBRAL DISK AND METHOD".

CROSS-REFERENCE TO RELATED APPLICATIONS

This application is related to U.S. Provisional Patent Application No. 60/422,039, filed Oct. 29, 2002, entitled "ARTIFICIAL VERTEBRAL DISK REPLACEMENT IMPLANT WITH TRANSLATING PIVOT PONT AND METHOD", U.S. patent No. 7,083,649, filed Oct. 14, 2003, entitled "ARTIFICIAL VERTEBRAL DISK REPLACEMENT IMPLANT WITH TRANSLATING PIVOT POINT AND METHOD, U.S. Provisional Patent Application No. 60/422,021, filed Oct. 29, 2002, entitled "ARTIFICIAL VERTEBRAL DISK REPLACEMENT IMPLANT WITH CROSSBAR SPACER AND METHOD", U.S. patent application Ser. No. 10/684,668, filed Oct. 14, 2003, entitled "ARTIFICIAL VERTEBRAL DISK REPLACEMENT IMPLANT WITH CROSSBAR SPACER AND METHOD", U.S. Provisional Patent Application No. 60/422,022, filed Oct. 29, 2002, entitled "ARTIFICIAL VERTEBRAL DISK REPLACEMENT IMPLANT WITH A SPACER AND METHOD", and U.S. Pat. No. 6,966,929, filed Oct. 14, 2003, entitled "ARTIFICIAL VERTEBRAL DISK REPLACEMENT IMPLANT WITH A SPACER", all of which are incorporated herein by reference.

FIELD OF THE INVENTION

This invention relates to tools for preparing vertebral bodies in the spine for the implantation of an artificial vertebral disk replacement and related method. This invention also relates to an artificial vertebral disk replacement, a method of operation, and a method of implanting.

BACKGROUND OF THE INVENTION

As the present society ages, it is anticipated that there will be an increase in degenerative and dysfunctional spinal disk conditions. Pain associated with such disk conditions can be relieved by medication and/or surgery.

Over the years, a variety of intervertebral implants have been developed in an effort to relieve the pain associated with such degenerative and dysfunctional disk conditions. For example, U.S. Pat. No. 4,349,921 to Kuntz discloses an intervertebral disk prosthesis. The Kuntz prosthesis is designed to restore the space between the disks.

U.S. Pat. No. 4,714,469 to Kenna discloses a spinal implant that fuses vertebrae to the implant. The implant has a rigid body that fits between the vertebrae with a protuberance extending from a vertebral contacting surface and into the vertebral body.

U.S. Pat. No. 5,258,031 to Salib et al. discloses another prosthetic disk with a ball that fits into a socket.

U.S. Pat. Nos. 5,425,773 and 5,562,738 are related patents to Boyd et al. that disclose a disk arthroplasty device for replacement of the spinal disk. A ball-and-socket are provided to enable rotation.

U.S. Pat. No. 5,534,029 to Shima discloses an articulated vertebral body spacer with a pair of upper and lower joint pieces inserted between the vertebrae. An intermediate layer is provided to allow for movement between the upper joint piece and the lower joint piece.

U.S. Pat. No. 5,782,832 to Larsen et al. discloses a two-piece ball-and-socket spinal implant with upper and lower plates for insertion within the intervertebral space.

U.S. Pat. No. 6,156,067 to Bryan et al. discloses a prosthesis having two plates with a nucleus therebetween.

None of these solutions provide an implant that restores a wide range of natural movement.

Accordingly, what is needed is an implant for alleviating such conditions and that restores natural movement.

SUMMARY OF THE INVENTION

The present invention includes embodiments that are directed to a set of tools used to implant an intervertebral disk replacement, and a method of placing the implant between vertebral bodies of the spine. A first tool is provided for use in preparing the vertebral bodies for the implant. A second tool is provided for installing the implant between the vertebral bodies.

Other aspects, objects, features, and elements of the other embodiments of the invention are described or are evident from the accompanying specification, claims and figures.

BRIEF DESCRIPTION OF THE DRAWINGS

FIG. 3A is a top view of a portion of an embodiment of the assembled implant of the invention. FIG. 3B is a top view of an embodiment of the implant of the invention showing a rotation to the right.

FIG. 4B is a perspective view of a socket portion of the embodiment of the implant of the invention.

FIG. 7A is a top view of an embodiment of a cutting tool of the invention used to prepare the vertebral bodies for the implant. FIG. 7B is a side view of the embodiment of the cutting tool of the invention.

FIG. 8A is a side view of an embodiment of the implant insertion tool of the invention. FIG. 8B is a top view of the embodiment of the implant insertion tool of the invention.

DETAILED DESCRIPTION OF THE PREFERRED EMBODIMENTS OF THE INVENTION

The following description is presented to enable any person skilled in the art to make and use the invention. Various modifications to the embodiments described will be readily apparent to those skilled in the art, and the principles defined herein can be applied to other embodiments and applications without departing from the spirit and scope of the present invention as defined by the appended claims. Thus, the present invention is not intended to be limited to the embodiments shown, but is to be accorded the widest scope consistent with the principles and features disclosed herein. To the extent necessary to achieve a complete understanding of the invention disclosed, the specification and drawings of all patents, patent publications, and patent applications cited in this application are incorporated herein by reference.

Figure 1A:
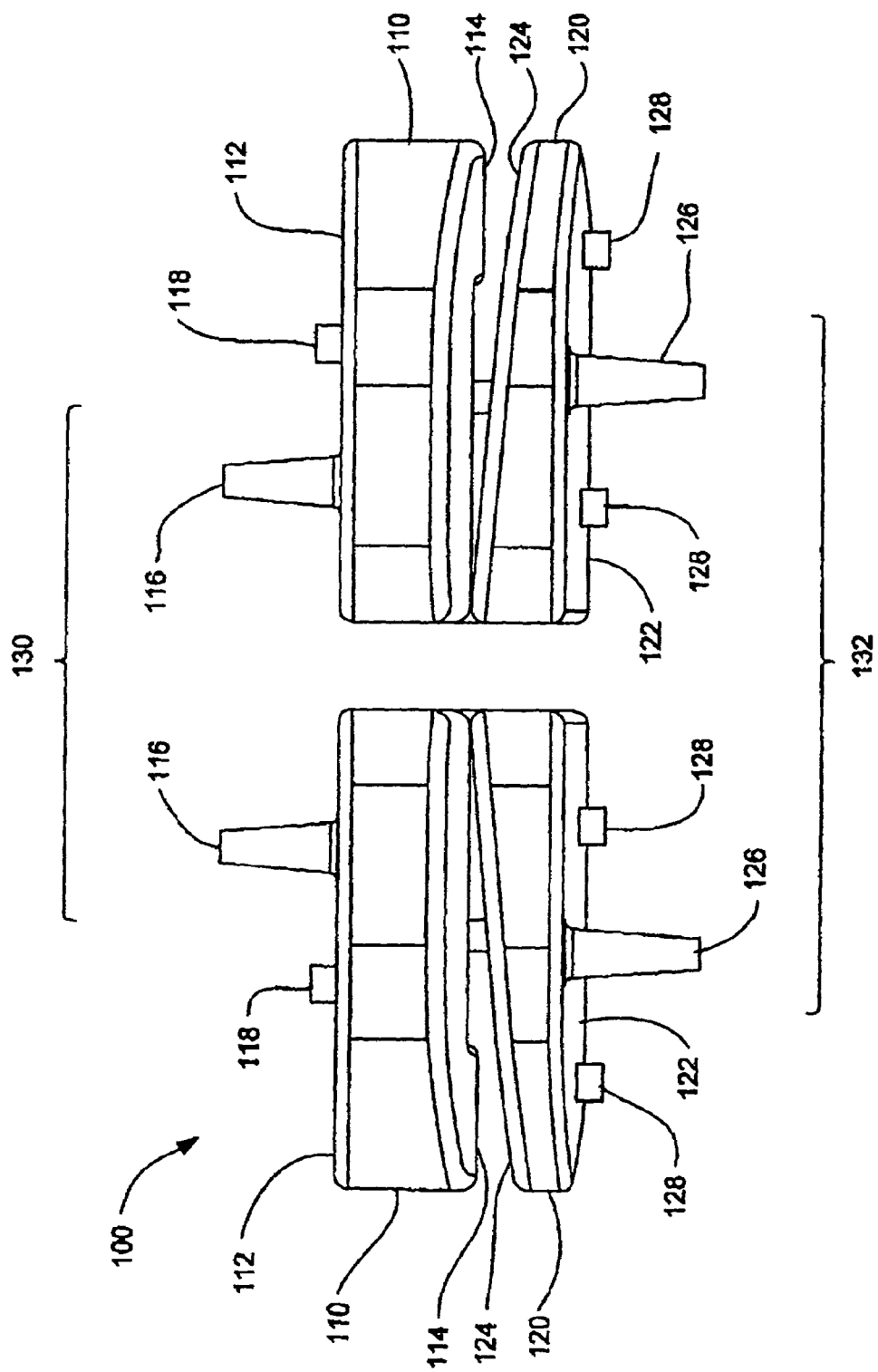
FIG. 1A is a posterior view of an embodiment of the assembled implant of the invention.

Turning now to FIG. 1A, a posterior view of an intervertebral implant 100 is depicted having a four-piece configuration. Although, as will be appreciated by those of skill in the art, other configurations, such as a two-piece configuration or a three-piece configuration, are possible without departing from the scope of the invention. As depicted, the intervertebral implant 100 has a pair 130 of first plates 110. Each first plate 110 has a first surface 112 and a second surface 114. The first surface 112 is configured to abut an end plate surface of a vertebral body. A keel 116 can be provided on the first surface 112 to anchor the first surface 112 into the vertebral body upon implantation. One or more additional protrusions 118 can also be provided that act as a detent or catch, thus providing a further mechanism to prevent the first plate 110 from moving relative to the vertebral body once implanted.

The intervertebral implant 100 also has a pair 132 of second plates 120. The second plates 120 have a first surface 122 and a second surface 124. The first surface 122 is configured to abut an end plate surface of a vertebral body. As with the first plate 110, a keel 126 can be provided on the first surface 122 to anchor the first surface 122 into the vertebral body upon implantation. One or more additional protrusions 128 can also be provided that act as a detent or catch, again providing a further mechanism to prevent the second plate 120 from moving relative to the vertebral body once implanted.

Figure 1B:
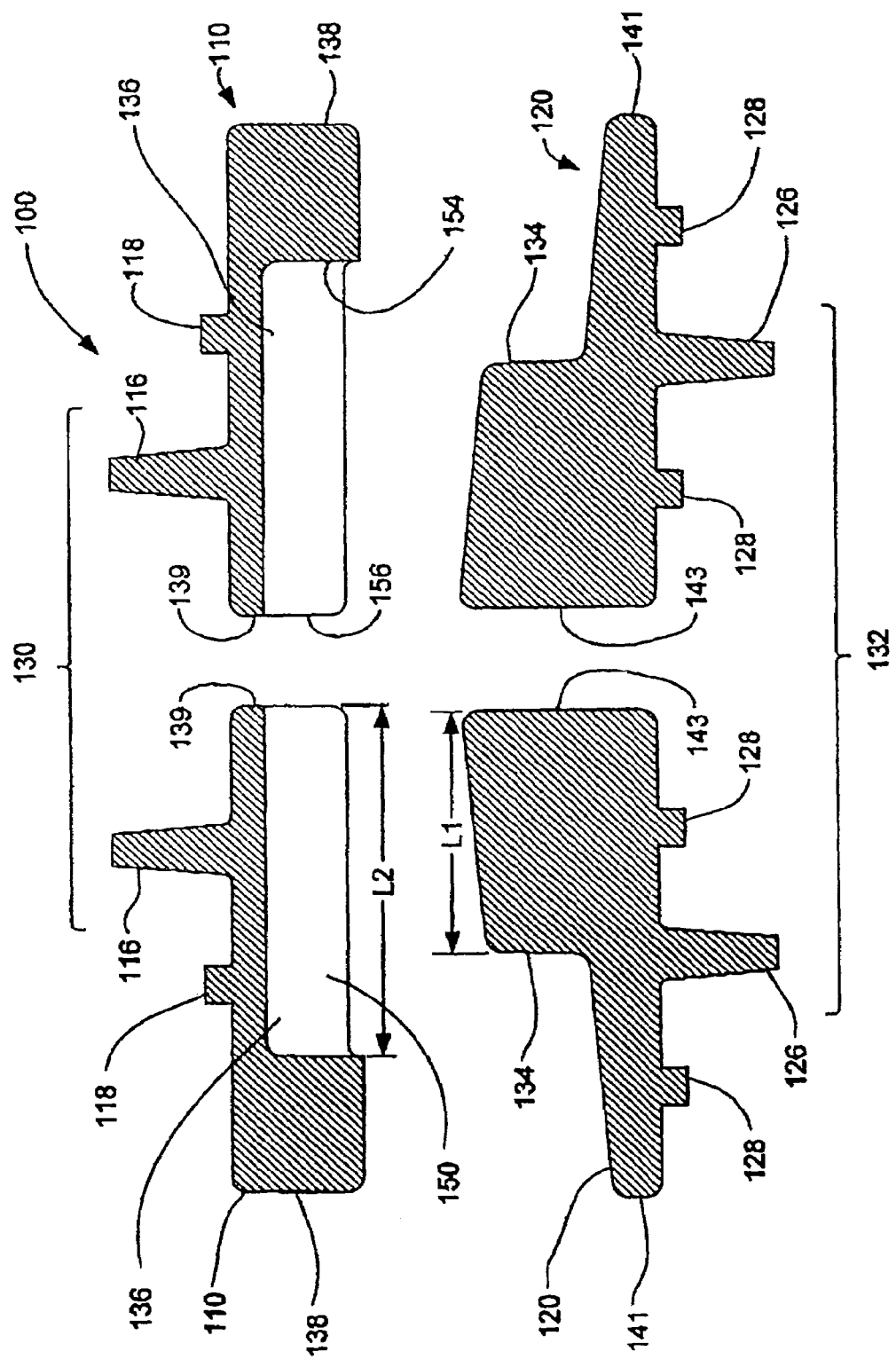
FIG. 1B is a cross-section of the device shown in FIG. 1A.

FIG. 1B depicts the pair 130 of upper plates 110 and the pair 132 of lower plates 120 in cross-section. Each upper plate 110 has a socket 136 that has a first elongated sidewall 150, a corresponding second elongated sidewall 152 (shown in FIG. 3B), an end wall 154, and an open end 156. The open ends 156 of each of the first plates 110 are oriented so that the open ends 156 face each other. The lower plates 120 each have a ball 134. As illustrated in FIG. 1B, the ball 134 is an elongated ball. Each of the plates 110, 120 has a first end 138, 141 and a second end 139, 143, respectively. The ends 139 of the first plate 110 face each other and the ends 143 of the second plate 120 also face each other. The ends 138, 141 are curved and convex, as shown in FIG. 3A, so that the implant 100 has a configuration that correlates to the curved shape of a vertebra.

Figure 1C:
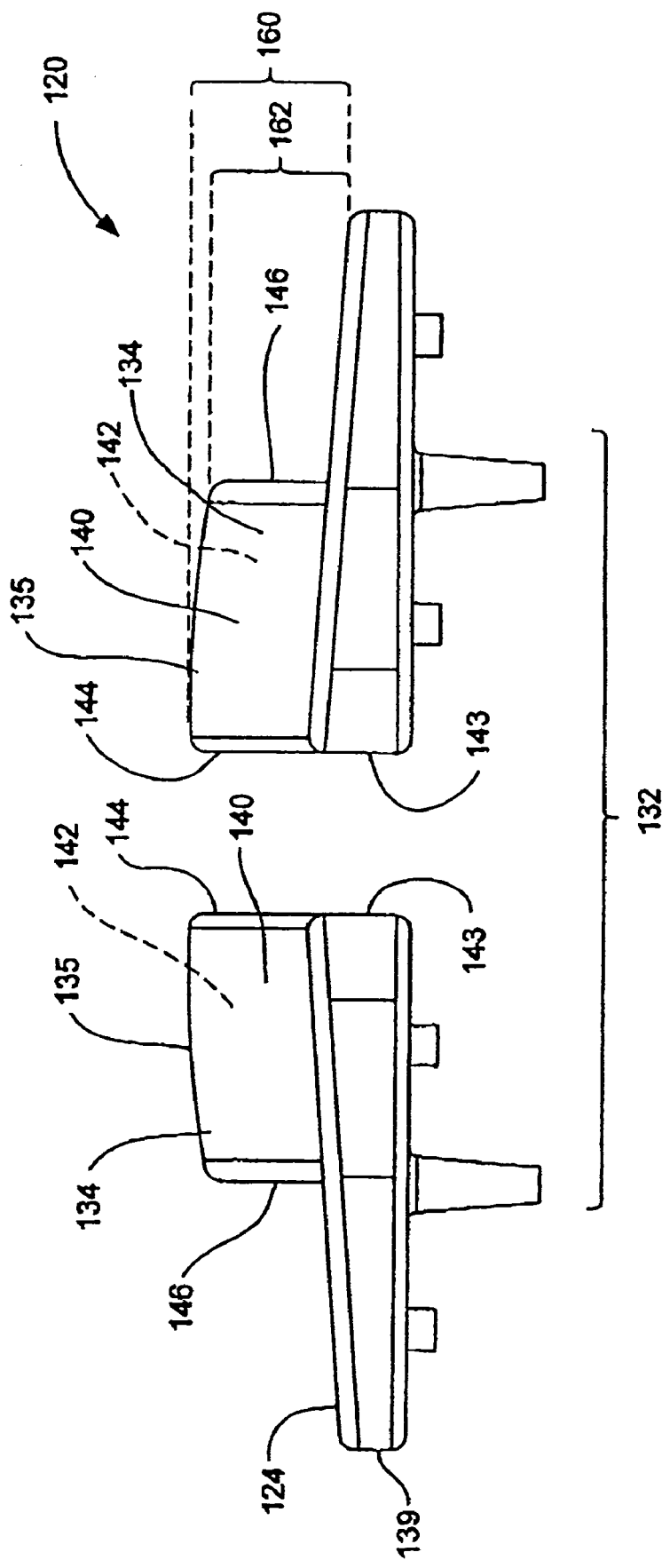
FIG. 1C is a posterior view of two bottom plates of the implant of the embodiment of the invention.

As shown in FIG. 1C, the ball 134 has four sides: a first elongated sidewall 140, a second elongated sidewall 142, a third end wall 144, and a fourth end wall 146. The third end wall 144 is flush with the end 143 of the plate 120 of the implant. The third end wall 144 has a profile height 160 and the fourth end wall 146 has a profile height 162. Comparing the profile heights 160, 162 to each other at the same point on the second surface 124 of the second plate 120, the overall profile height of the third end wall 144 is greater than the fourth end wall 146 (i.e., 160>162). Thus, it is evident that the upper surface 135 of socket 136 slopes downwardly from the end wall 144 to the end wall 146. Together balls 134 comprise a ball structure that has a high surface where the third end walls 144 abut each other and slope to a lower surface adjacent to fourth end walls 146. Also, preferably, the upper surfaces 135 are barrel shaped and have a "U" shaped profile along a cross-section that is perpendicular to the page of FIG. 1C (parallel the sagittal plane on implantation). The sloping upper surface 135, as will be explained later, allows the pair 130 of upper plates 110 to easily slide, or rock, side-to-side on the ball structure and slide, or ride, forward and backward with enough looseness of fit to allow for some twisting in order to emulate the motion of the vertebral bone and intervertebral disk tissue. This arrangement, thus, has a sliding or translating pivot point. Further, as indicated in FIG. 1C, the edges are eased or rounded to allow for further range of motion of the pair 130 of plates 110 relative to the pair 132 of plates 120. As will be appreciated by those of skill in the art, the overall height of the third end wall 144 and the fourth end wall 146 can be equivalent while still having an effective third end wall height 160 that is greater than the effective fourth end wall height 162 due to the overall slope of the second surface 124. Alternatively, the overall height of the third end wall 144 and the fourth end wall 146, can be different with the third end wall 144 having a height greater than the fourth end wall 146, thus eliminating the need for the second surface 124 to have a slope or further increasing the net difference between the height of the third end wall and the fourth end wall.

Further, although the ball 134 is depicted such that the third end wall 144 is flush with the second end 143, those of skill in the art will appreciate that the ball 134 could also be configured such that the third end wall 144 was recessed relative to the end 143 of the second plate. In such a configuration, the third end wall 144 and the end 143 would not be flush.

Figure 1D:
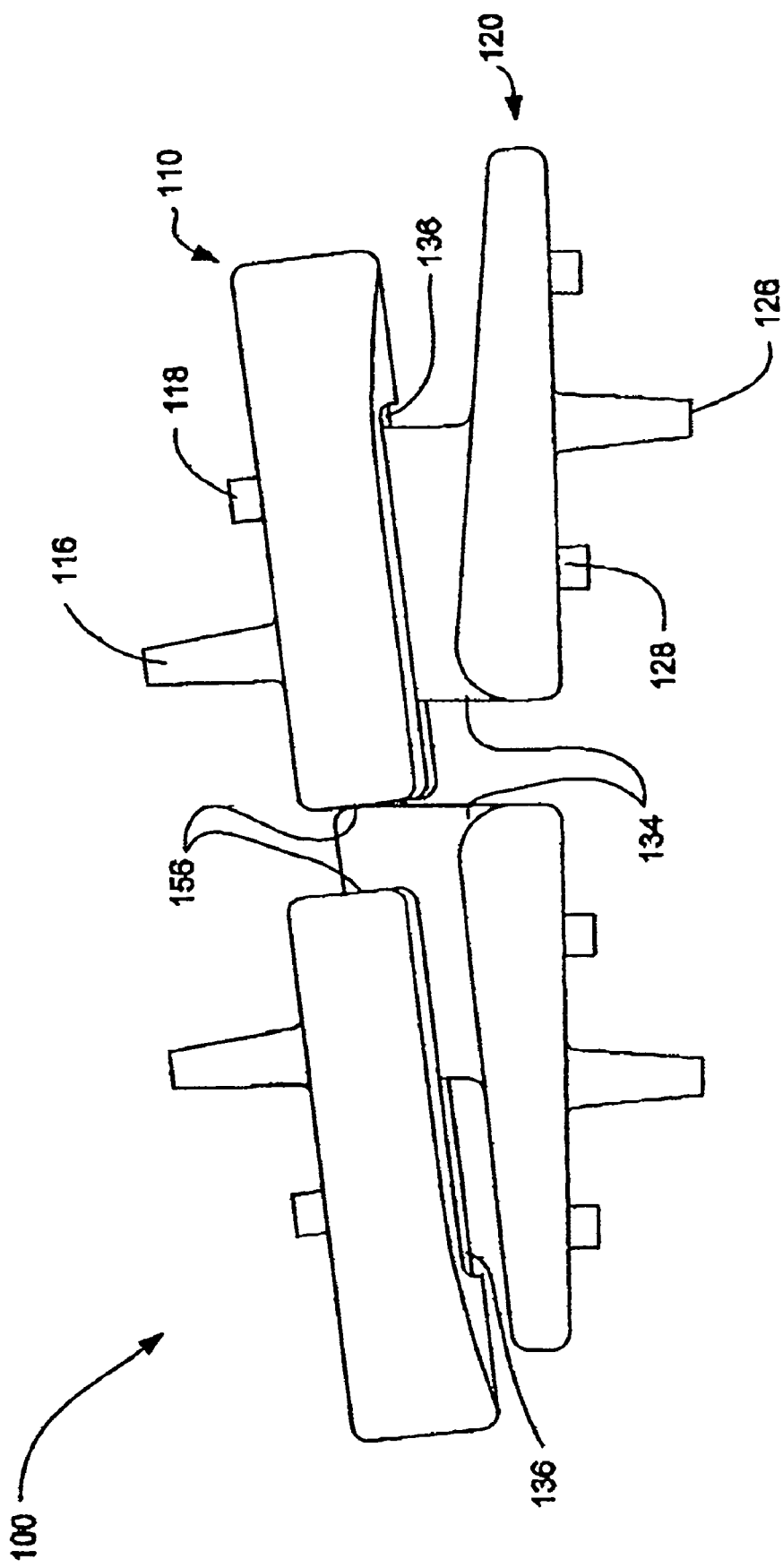
FIGS. 1D and 1E are posterior views of the embodiment of the implant of the invention shown in FIG. 1A illustrating the operation of the device in bending to the left and bending to the right, respectively.
Figure 1E:
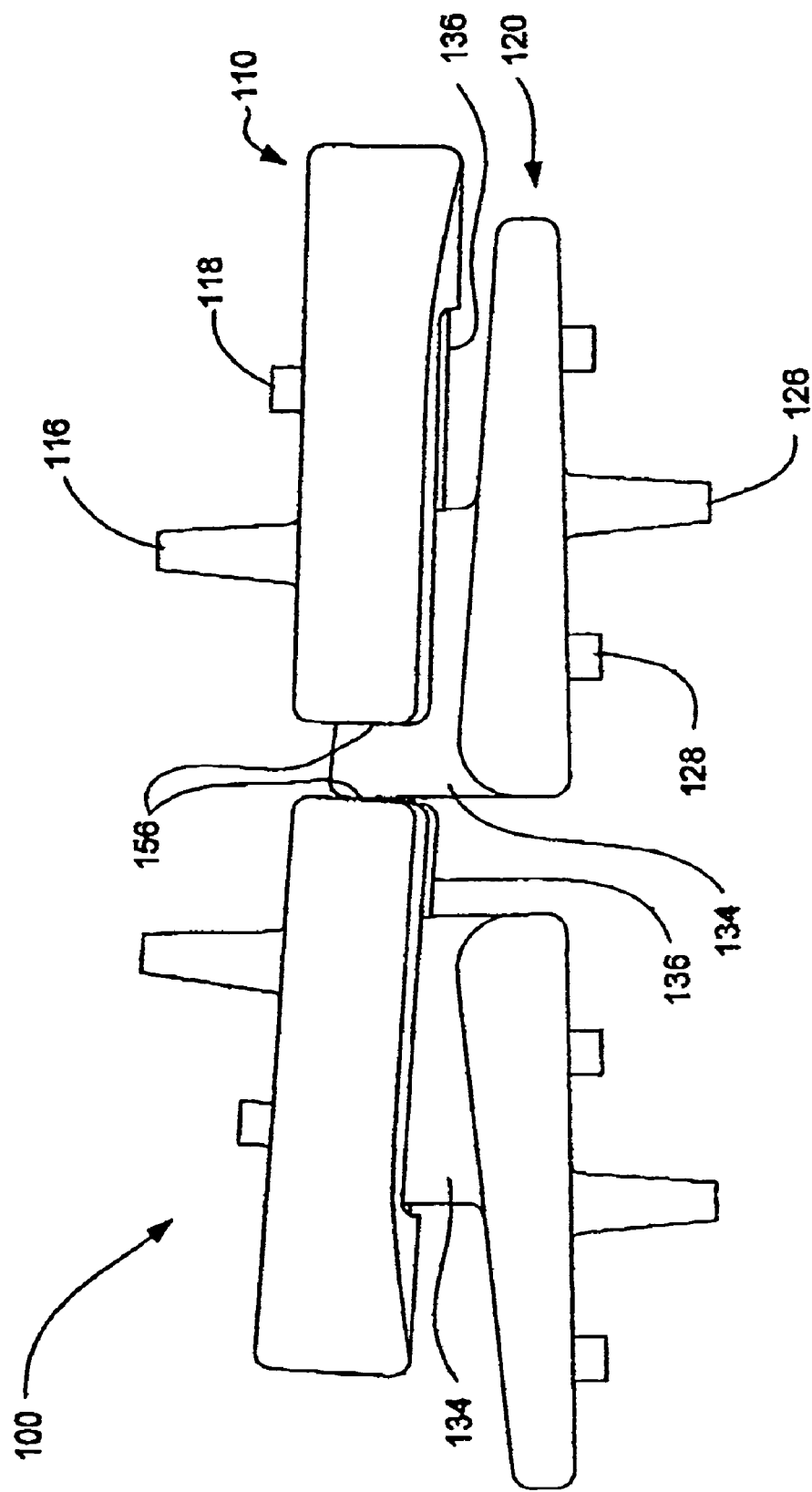

FIGS. 1D and 1E illustrate posterior views of the implant 100 showing the clearance for left and right lateral bending. Typically, left and right lateral bending ranges from 3-5°. As evident from these figures (and FIG. 1B), the length L1 of the ball 134 can be less than the length L2 of the socket 136. Further, as shown, the open ends 156 of the sockets facilitate movement of the balls 134 within the socket 136 to accommodate side-bending movement.

Figure 2A:
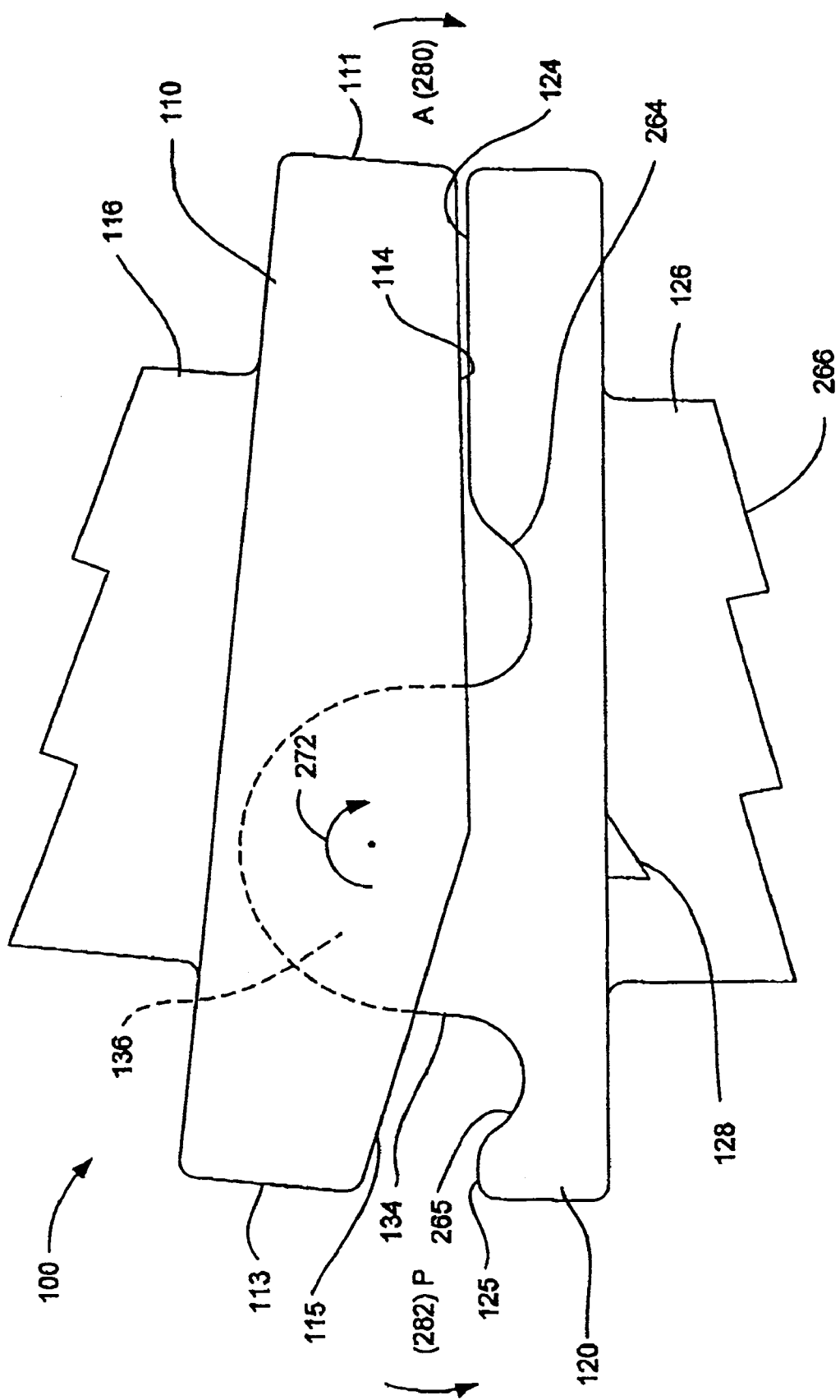
FIG. 2A is a side view of the implant of FIG. 1A showing the implant in flexion.

FIG. 2A is a side view of the intervertebral implant 100. The first plate 110 with this socket 136 and the second plate 120 with the ball portion 134 are depicted. As is apparent from the figure, the sloping of the second surface 114 of the first plate 110 facilitates rotation of the ball-and-socket joint in an anterior "A" 280 direction and a posterior "P" 282 direction. As depicted, the second surface 114 slopes from a high point at about where the socket is located to low points at the ends 111 and 113 of the plate 110. As shown in FIG. 2A, the implant 100 is positioned to achieve flexion 272 (i.e., forward bending) in a range up to about 15°, but more preferably 10°.

As shown in FIG. 2A, the second plate 120 can also have channels 264, 265 or a groove adjacent the ball 134. The channels 264, 265 can be configured such that it surrounds a portion of the ball 134 or the entire ball 134. As will be explained below, the channel allows the sides of the ball 134 to be made more perpendicular so as to create a greater blocking wall thus preventing the socket of the upper plate 100 from moving too much anteriorly or posteriorly relative to the lower plate 120.

Either one or both of the keels on the first surface 116 and the second surface 126 can have one or more posteriorly pointing teeth 266 to enable it to more securely engage the vertebral body into which it is implanted. As can be seen in FIG. 2A, the protrusions 128, as well as the additional protrusions 118 (FIG. 1A) can also have posteriorly pointing teeth in order to lock the implant 100 in position in the vertebrae.

Figure 2B:
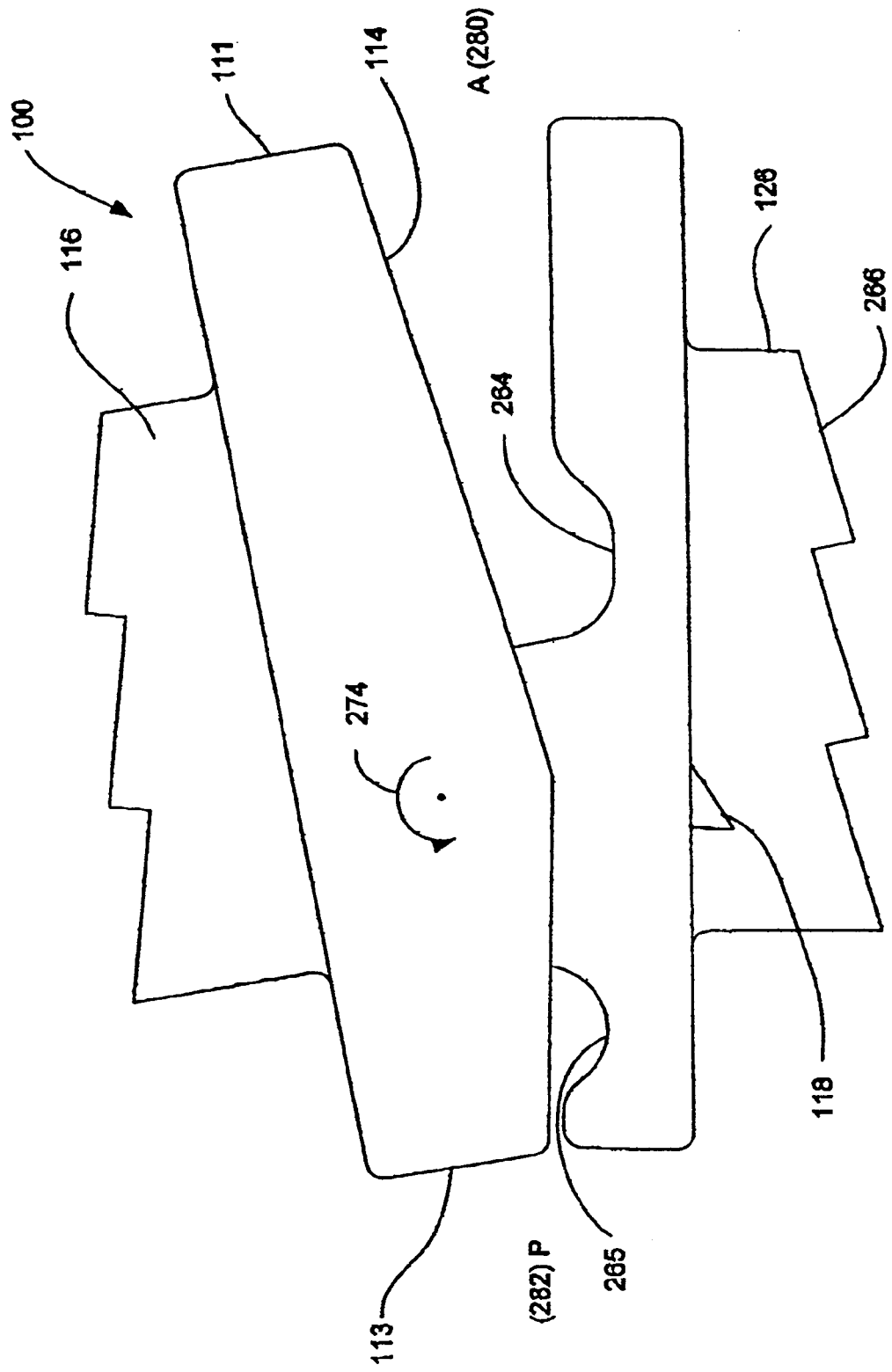
FIG. 2B is a side view of the implant showing the implant in extension.

FIG. 2B is an alternate side view of the intervertebral implant 100 wherein the plates 110, 120 are shown and the ball-and-socket joint is positioned to achieve extension 274 (i.e., backward bending) in a preferable range of up to about 5°.

Figure 2C:
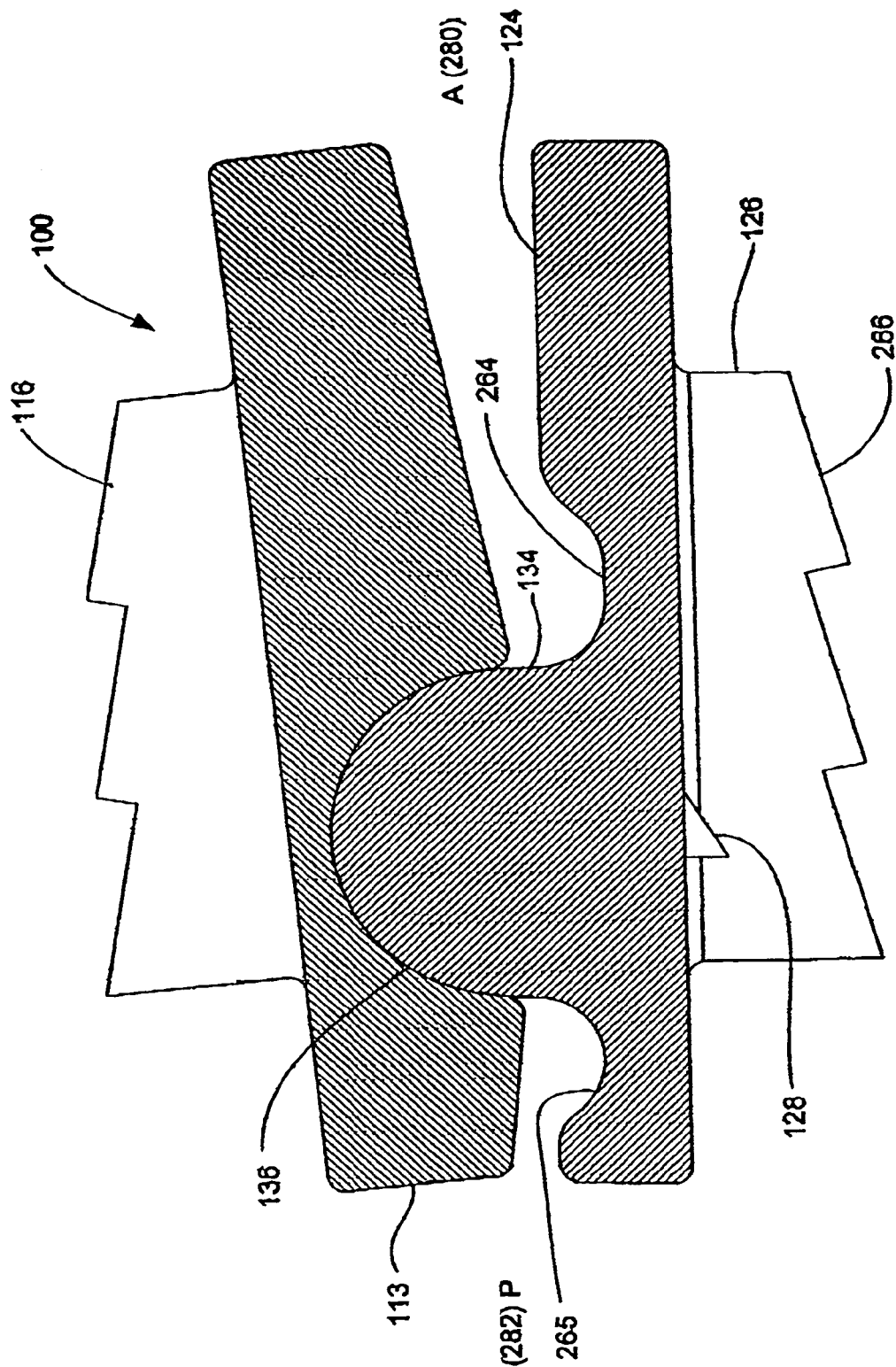
FIG. 2C is a partial cross-sectional view of a side view of the implant of an embodiment of the invention.
Figure 2D:
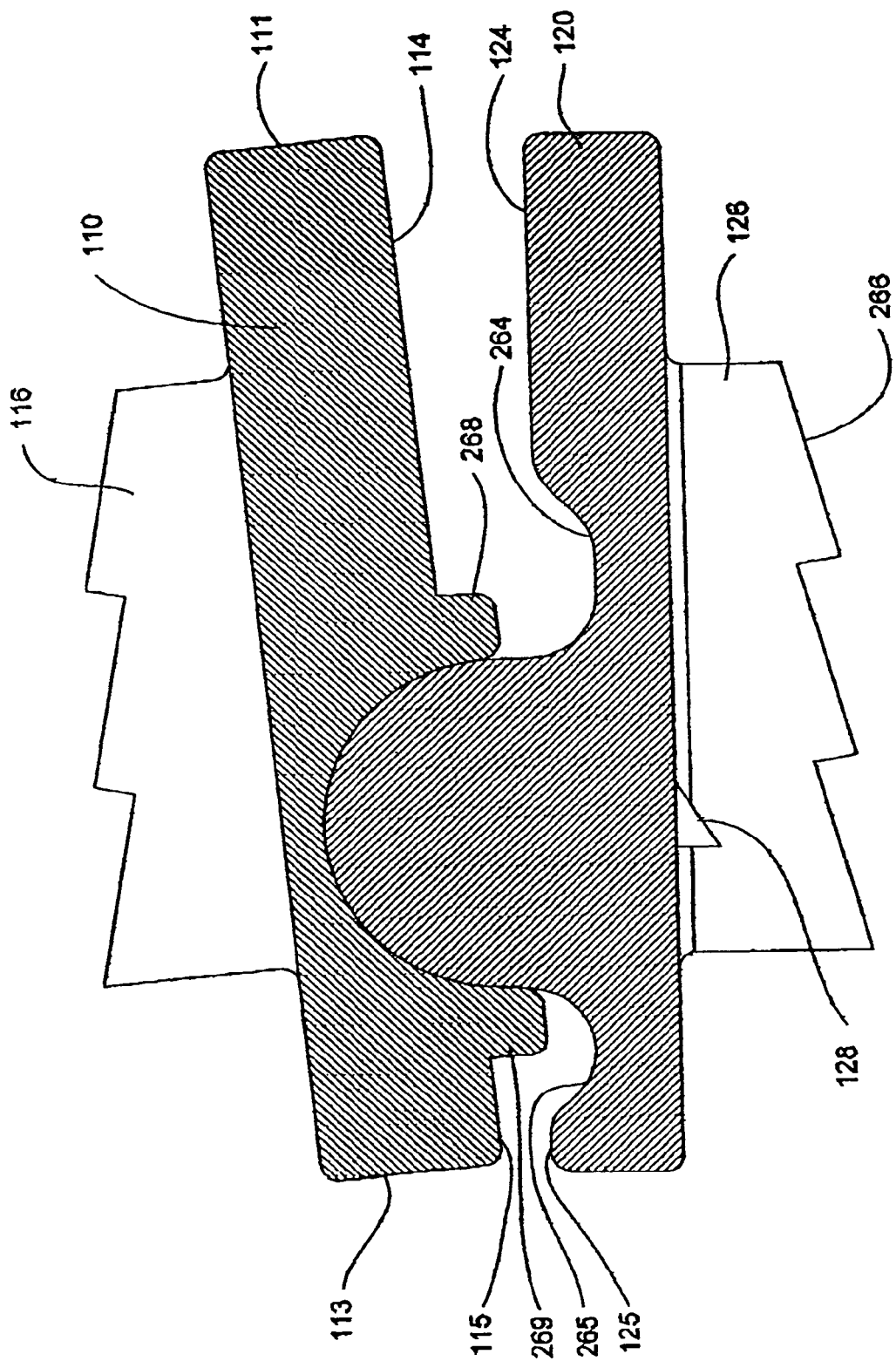
FIG. 2D is a partial cross-sectional view of an alternative embodiment of the implant of the invention having a protuberance adjacent the socket.

FIG. 2C is a cross-section of the side view of the intervertebral implant 100 showing the mating of the ball 134 to the socket 136. FIG. 2D illustrates an alternate embodiment of the first plate 110 wherein the socket 136 has ridges 268, 269 forming a protuberance that extends into the channel 264, 265 respectively on the second plate 120. As will be appreciated by those of skill in the art, the protuberances 268, 269 can extend partially into the channel, such as the configuration shown, or can have a channel conforming shape such that when the ball-and-socket joint are moved to achieve flexion 272 or extension 274 the protuberance or ridge 268, 269 extends into the channels 264, 265. This embodiment allows the surfaces 114 and 115 of the first plate 110 and the second plate 115 to be flat and non-sloping as shown while still allowing for the implant to emulate forward and backward bending and allow for the blocking of the motion of the socket relative to the ball.

Turning now to FIG. 3A, a top view of one-half of the intervertebral implant 100 is shown. Each of the top first plate 110 and the bottom second plate 120 have a bore 376 for receiving a pin of an implant tool. The keel 116 on the first plate 110 is positioned so that it is does not align in the same plane with the keel 126 on the second plate 120. As will be explained in further detail later, the non-alignment allows for the implant including the keels to be properly positioned between the vertebrae in such a way to accommodate the position of the nerves as the nerves extend out from the between adjacent vertebrae. Additionally, the length of ball 134 from the third end wall 144 to the fourth end wall 146 is shorter than the length of the socket 136 from the end wall 154 to the open end 156 as discussed before.

Figure 3C:
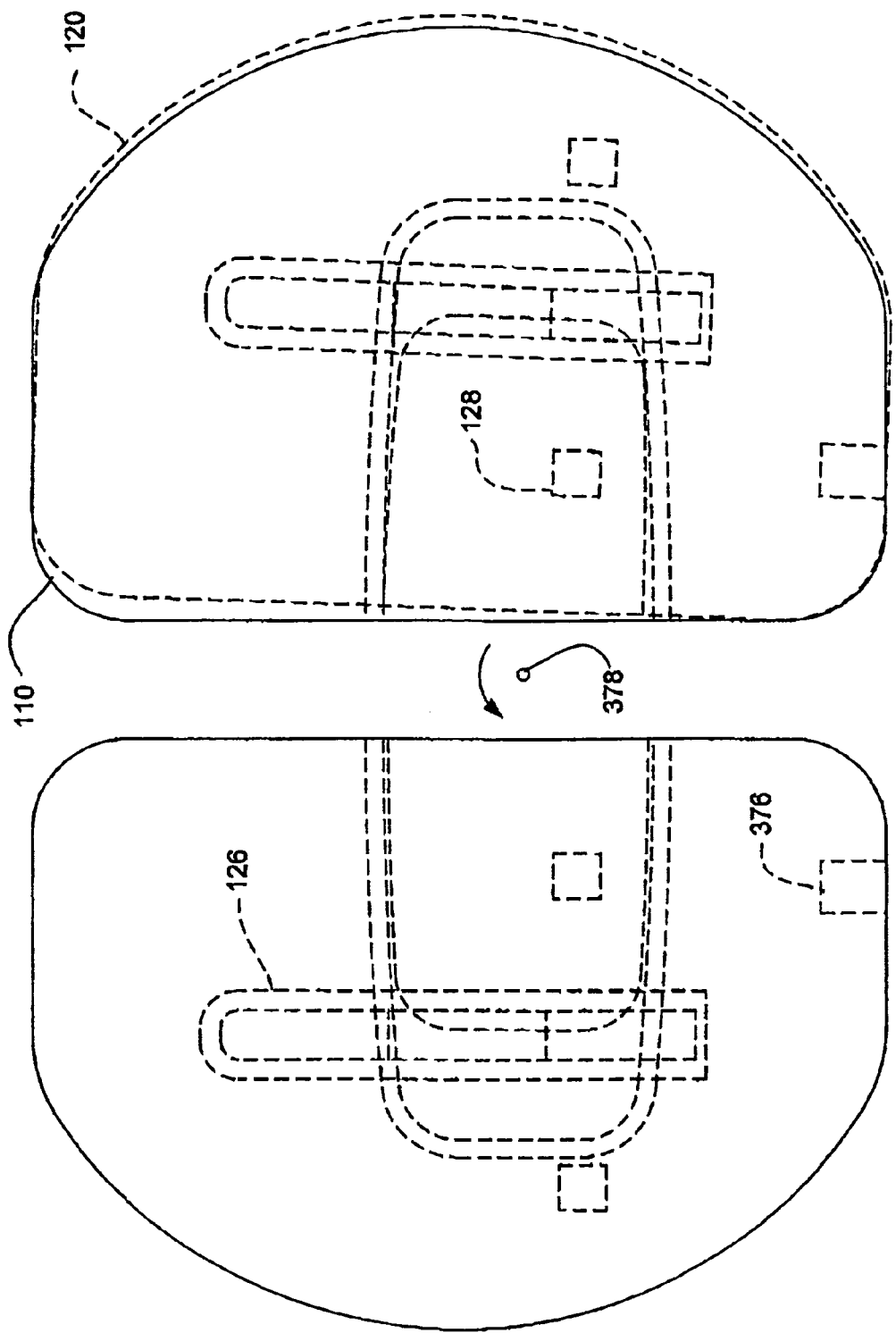
FIG. 3C is a top view of an embodiment of the implant of the invention showing a rotation to the left.

FIGS. 3B and 3C show the relative rotation of the upper first plate 110 to the lower second plate 120 to achieve rotation about a central axis 378. This rotation results in about a 3°-6° rotation about the axis (i.e., 3° of torso twisting in each direction).

Figure 4A:
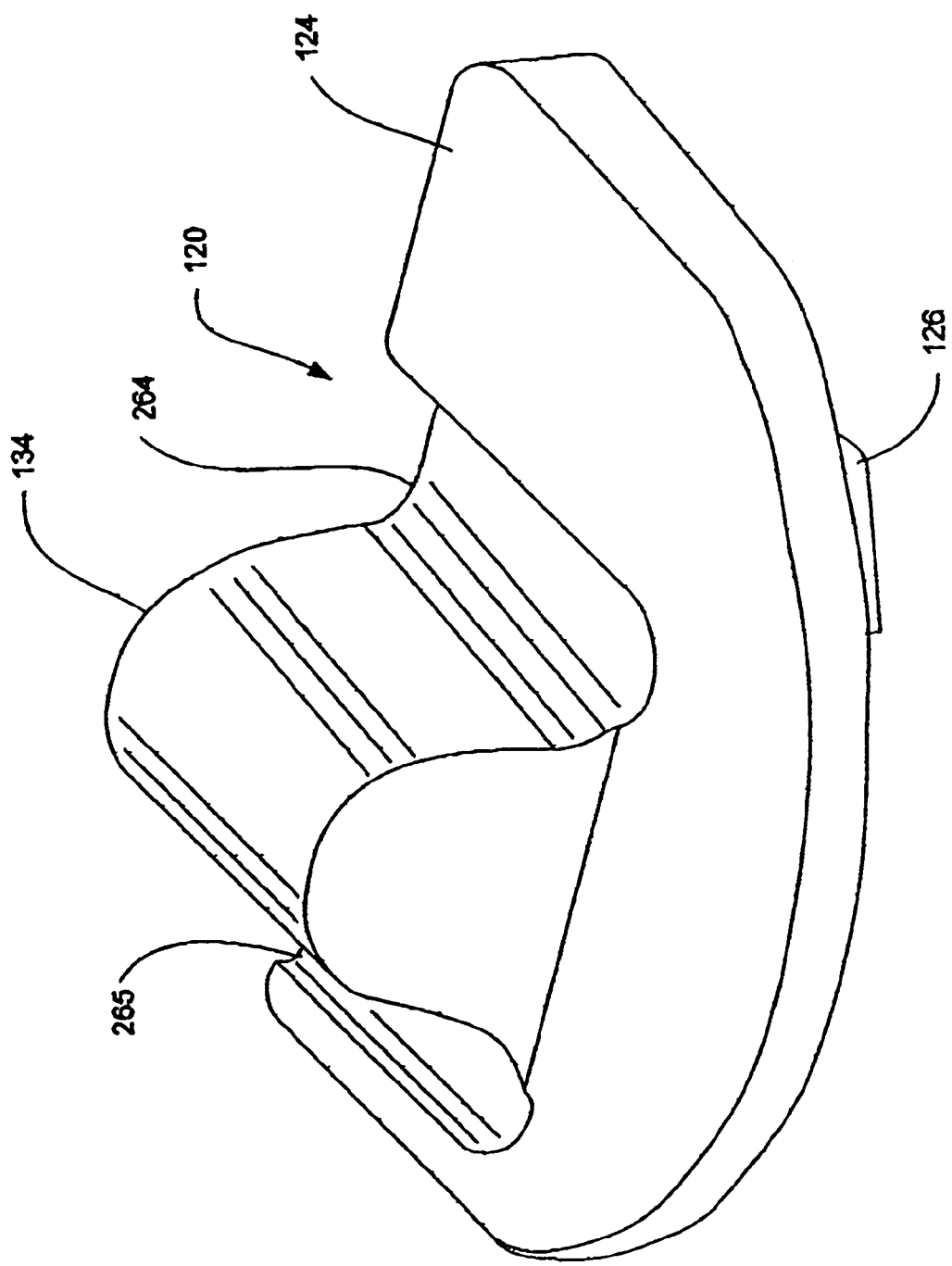
FIG. 4A is a perspective view of a ball portion of the embodiment of the implant of the invention.

FIG. 4A shows a perspective view of a second plate 120 of the intervertebral implant 100. The second surface 124 of the second plate 120 with the ball 134 and channels or grooves 264, 265 extending thereabout. As illustrated in FIG. 4A, the channels 264, 265 are formed on two sides of the ball 134. However, as will be appreciated by those of skill in the art, the channels 264, 265 can alternatively surround the ball 134.

FIG. 4B shows a perspective view of the first plate 110. The first plate 110 has a second surface 114, as described above, and, extending therefrom is the socket 136 therein. The socket 136 of FIG. 4B is configured to mate with the ball 134 of FIG. 4A, as described above.

Figure 5A:
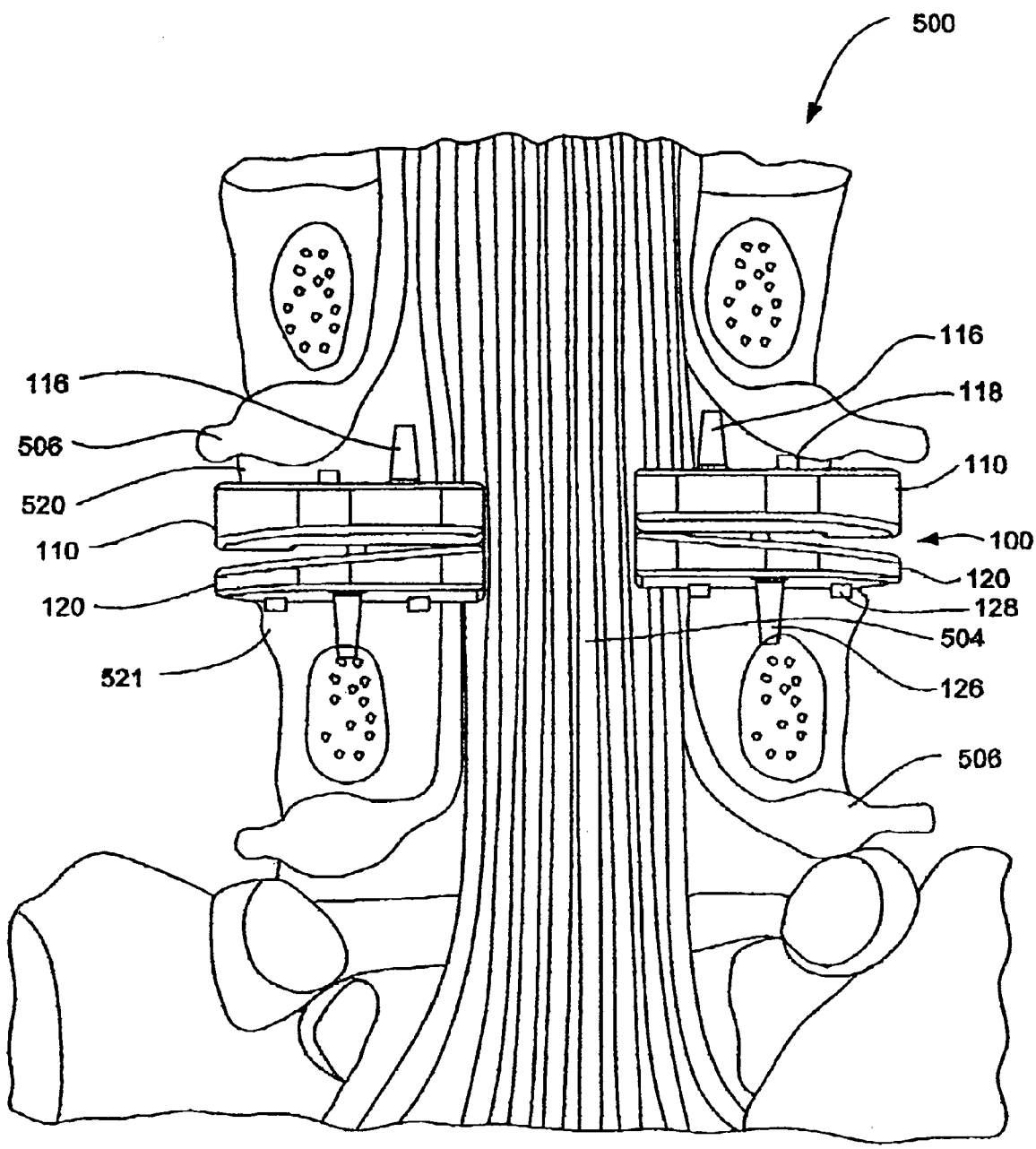
FIG. 5A is a posterior view of the embodiment of the implant of the invention after being implanted between two vertebral bodies.

FIG. 5A illustrates a posterior view of the implant shown in FIG. 1A implanted between vertebral bodies in a spine. FIG. 5A illustrates the spinal column 500 and the cauda equina 504 (a collection of lumbar and sacral nerve roots that fill the caudal end of the spinal cord) with individual nerves 506 exiting the cord between lumbar vertebrae. The implant 100 is positioned between two vertebral bodies 520, 521 such that the keels 116, 126 do not interfere with the cauda equina 504 and the exiting nerve 506. As can be seen in FIG. 5A, the keel 116 of the upper first plates 110 are close together and inboard of the keel 126 of the lower second plate 120. This allows the lower keels 126 to be clear of the nerves 506 as the nerves exit from between the adjacent vertebrae.

Figure 5B:
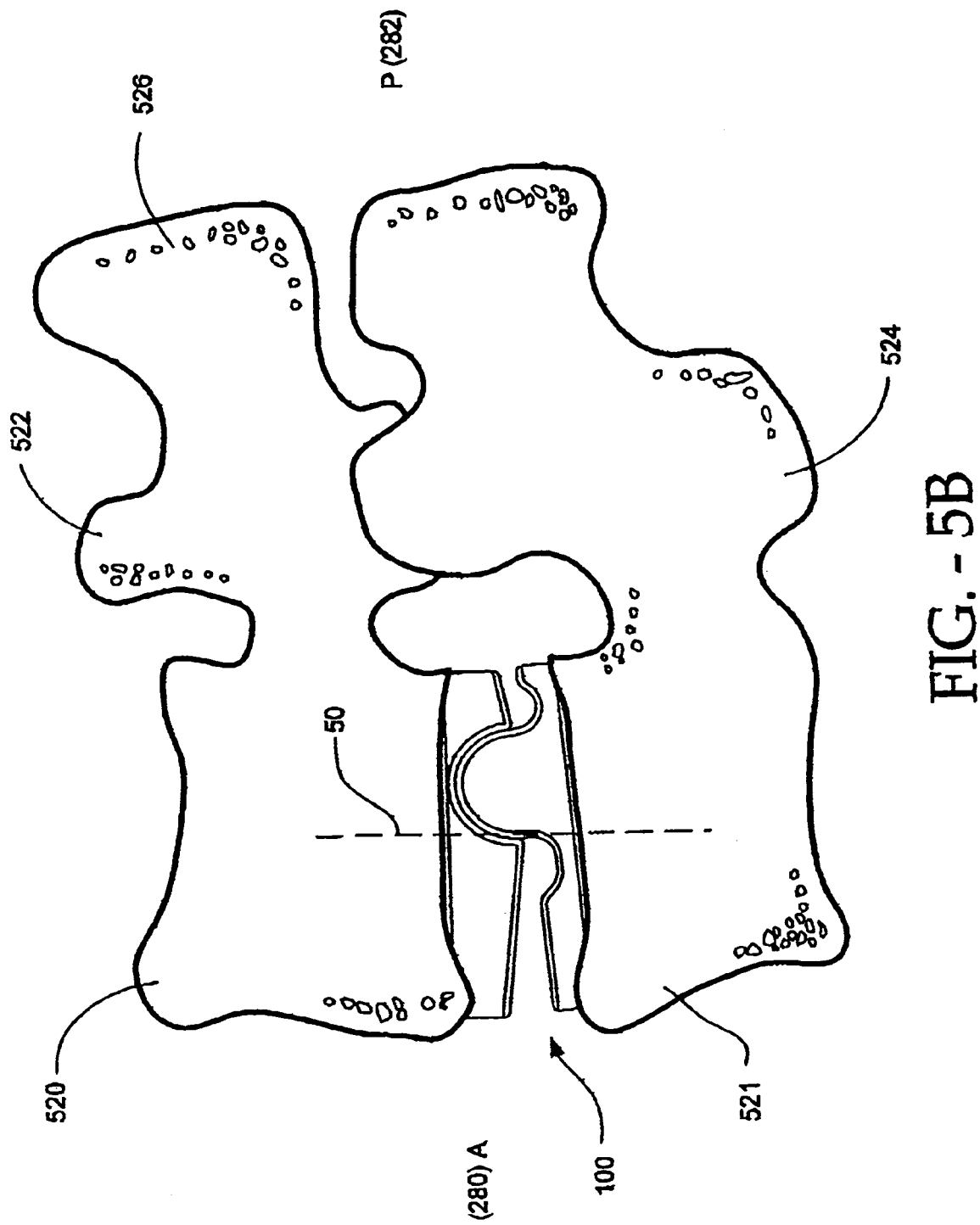
FIG. 5B is a side view of the embodiment of the implant of the invention after being implanted between two vertebral bodies.

FIG. 5B illustrates a side view of the implant 100, such as that shown in FIG. 1A, implanted between vertebral bodies 520, 521. The implant 100 is implanted so that the ball-and-socket joint enables about a 5° extension (backward bending) and about a 10° flexion (forward bending). In this view the ball and socket arrangement crosses the centerline 50 of the implant 100 and extends in a posterior 282 direction. In this embodiment, the ball-and-socket arrangement can be more centered on the centerline 50 or extend from a position when the implant 100 crosses the centerline 50 and extends in an anterior 280 direction. Further, in another preferred embodiment, the ball can be approximately bisected by the centerline.

Figure 6:
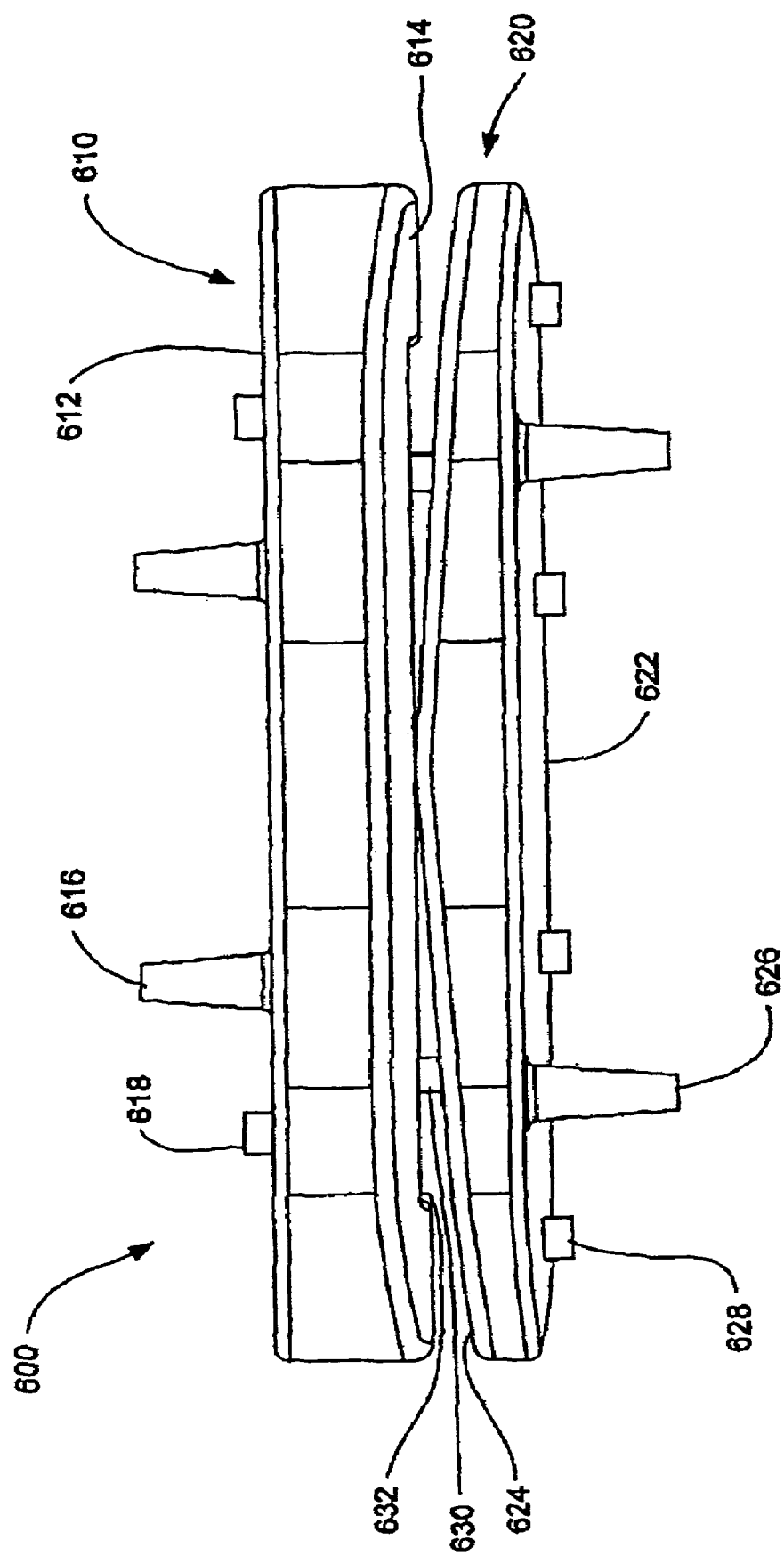
FIG. 6 is a rear view of an alternate embodiment of the invention having two plates.

FIG. 6 illustrates a rear view of an alternate embodiment of the implant shown in FIG. 1A. The implant 600 of FIG. 6 is in the form of a two-piece implant 600 having a first plate 610 and a second plate 620. The first plate 610 has a first surface 612 that contacts the vertebral body and has one or more keels 616 and detents 618 for anchoring the first plate 610 into the vertebral body. The implant 600 also has a second plate 620 that has a first surface 622 that contacts the vertebral body and has one or more keels 626 and detents 628 for anchoring the second plate 620 into the vertebral body. The second surface 614 of the first plate 610 has a socket 632 formed therein while the second surface 624 of the second plate 620 has a ball 630. This implant 600 moves in much the same way as implant 100 described above.

As will be appreciated by those of skill in the art, implant 100 is predominantly designed for a posterior implantation method. However, implant 100 can also be implanted from an anterior direction. Implant 600 is designed for predominantly an anterior implantation approach.

Further, a combination of the two embodiments shown in FIG. 1A and FIG. 6 can be used to create a three-piece implant as will also be appreciated by those of skill in the art. For example, the first plate 610 of FIG. 6 with its socket 632 can be combined with two-second plates 120 of FIG. 1A to form an implant. Similarly, the second plate 620 of FIG. 6 and its ball 630 can be combined with two first plates 110 from FIG. 1A to achieve an implant. Neither of these configurations depart from the scope of the invention. It is also to be understood that the implant 100, 600 can be comprised of any suitable biocompatible material, such as titanium.

Figure 7C:
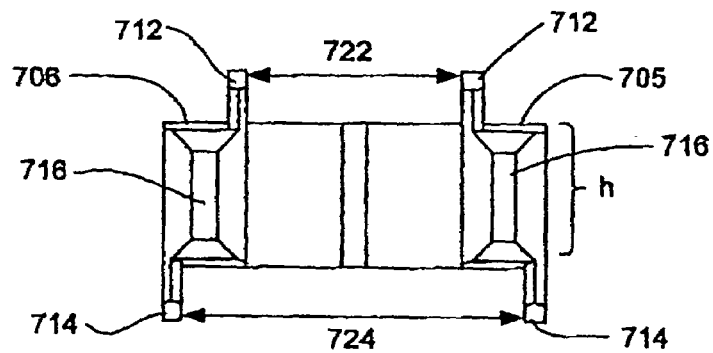
FIG. 7C is a distal end view of an embodiment of the cutting tool of the invention.
Figures 7D, 7E:
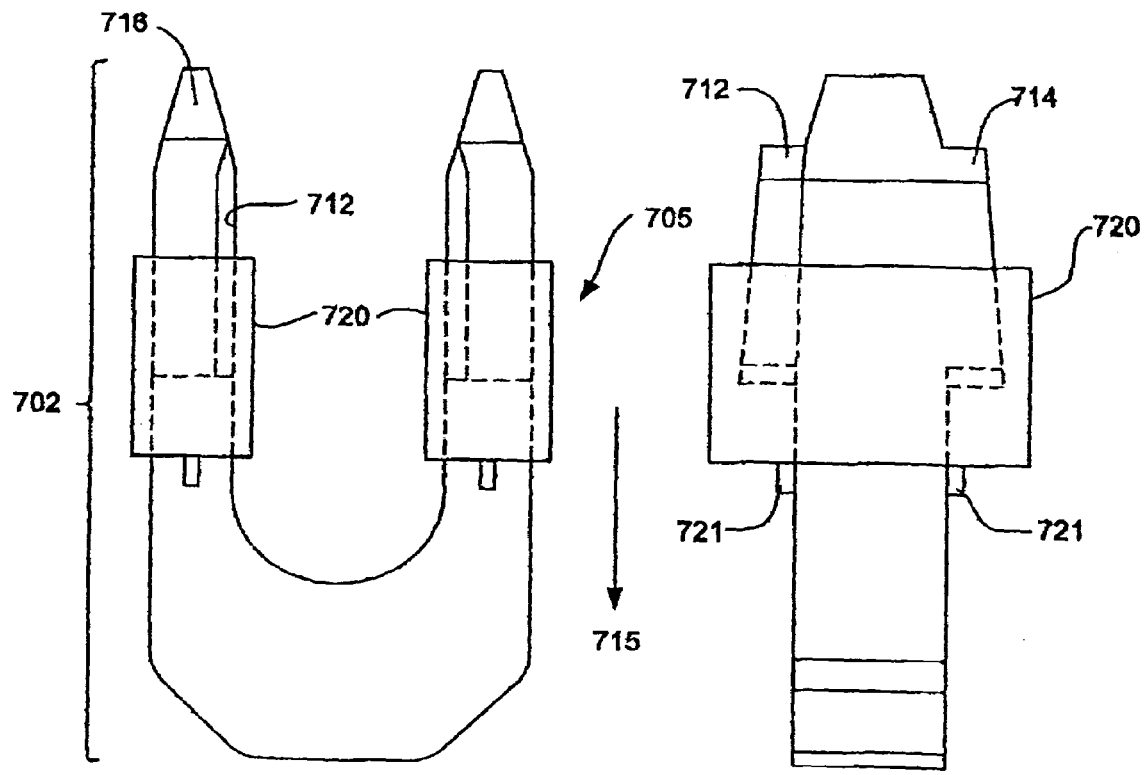
FIG. 7D is a top view of the cutting portion of an alternative embodiment of the cutting tool of the invention showing blade protectors.
FIG. 7E is a side view of the cutting portion of an alternative embodiment of the cutting tool of the invention showing the blade protectors.
Figure 8C:
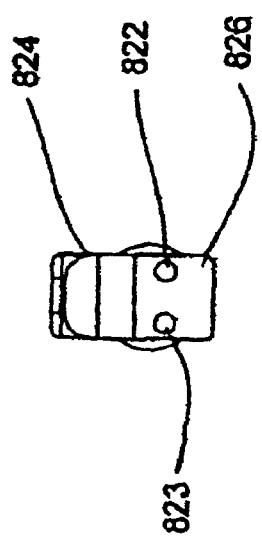
FIG. 8C is a distal end view of the embodiment of the implant insertion tool of the invention.
Figure 8D:
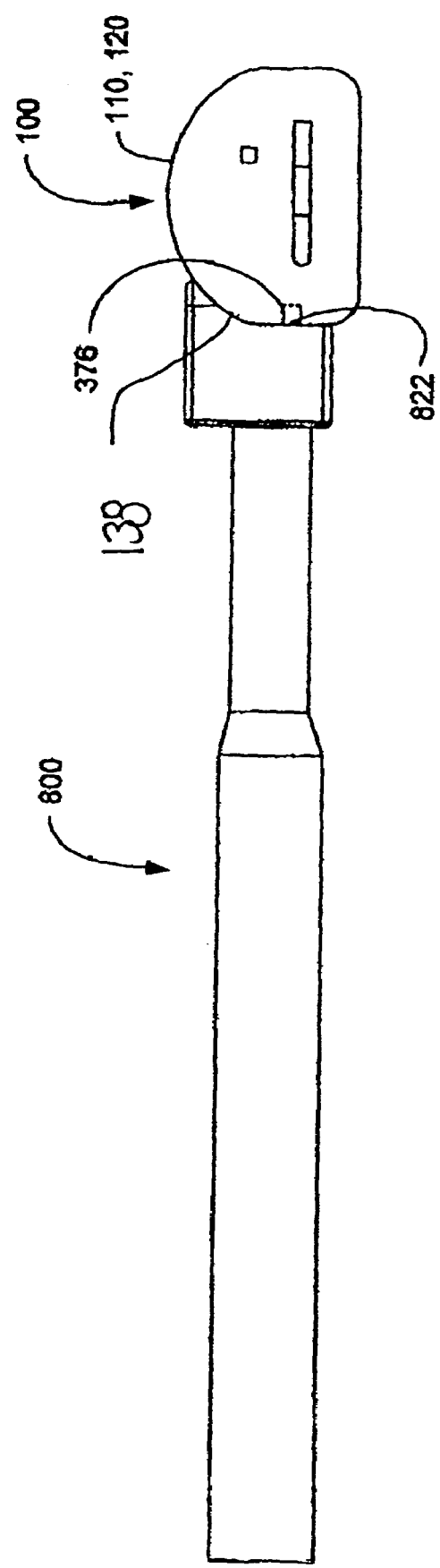
FIG. 8D is a top view of an embodiment of the implant insertion tool holding an embodiment of the implant.

Turning now to FIGS. 7 and 8 and the tools for preparing the vertebral bodies and implanting the implant 100 as described. FIG. 7A depicts a top view of a cutting tool 700 used to prepare the vertebral bodies for the implant 100 and FIG. 7B depicts a side view of tool 700. The cutting tool 700 has a handle 710 at its proximal end for controlling the tool during operation. As will be appreciated by those of skill in the art, the handle 710 can be removable or affixed to the cutting end.

The distal end 702 of the tool 700 is forked to form two prongs or tines 705, 706. The end of each tine 705, 706 has a beveled edge 716 at its distal most end. Each tine 705, 706 also has an inner blade 712 located on an inner upper side and an outer blade 714 located on an outer lower side (shown in FIG. 7C). Preferably the inner blades 712 are coplanar with the surface of the inner side of the tine and the outer blades 714 are coplanar with the outer side of the tine. The inner blades 712 are oriented to cut a space in a first intervertebral body for the first surface keel 116 of the implant and the outer blades 714 are oriented to cut a space in the facing intervertebral body for the second surface keel 126. The orientation of the blades is such that each of the cuts made for the keels of the implant are offset and avoid the nerves in the cauda equina or exiting the cauda equina.

FIG. 7C is a view of the distal end of the cutting tool 700 showing the beveled edges 716 of the tines 705, 706 and the inner blades 712 and outer blades 714. The distance 722 between the inner blades 712 is less than the distance 724 between the outer blades and the height h of the tines approximates the distance between two vertebral bodies or the height of the disk space. The blades 712, 714 extend above and below the tines or the height of the tines. As can be seen in FIG. 7C, the beveled sides of the distal end 716 extend and form at least one of the beveled sides of the blades 712, 714.

FIG. 7D depicts an enlarged top view of the tines 705, 706 of the distal end of cutting tool 700 with the beveled distal edges 716. FIG. 7E is an enlarged side view of the distal end of cutting tool 700. FIGS. 7D and 7E show the retractable blade protector 720 for the blade 712 positioned in a retracted position. As the cutting tool is inserted between vertebral bodies, the retractable blade protector 720 moves in a posterior direction 715 (i.e., toward the handle 710) to expose the inner blade 712 and the outer blade 714 and to enable the blades to cut into the vertebral bodies. These protectors 720 can be spring biased as desired in order to cover the blade 712, 714 as the tool 700 is inserted past the nerves. The protectors 720 are urged in a posterior direction as the blades 712, 714 are urged into the vertebral bodies in order to cut channels for the keels. Springs 721 provide the desired bias to keep the protectors 720 in a forward position covering the blades 712, 718.

As will be appreciated by those of skill in the art, the tool shown in FIG. 7 can be modified such that instead of cutting keel-receiving channels in the upper and lower vertebral bodies at the same time, two tools are provided so that only one vertebral body is cut for keel-receiving channels at a time. For example, a first tool having two tines as described above could be provided having a pair of inner blades located on an upper surface of the tines. A second tool could be provided having tines as described with a pair of outer blades located on the lower surface of the tines. Optionally, the second tool can have a guide corresponding to the location of the first blade on the first tool to ensure that the second cut is optimally aligned with the first cut. In use, a pair of channels can be cut into the upper vertebral body using the first tool. Thereafter a second pair of channels can be cut into the lower vertebral body. Alternate arrangements are also possible, for example, where the first tool has a pair of outer blades and the second tool has a pair of inner blades, or where the first tool has upper and lower blades on a first tine (e.g., right tine) and the second tool has upper and lower blades on a second tine (e.g., left tine).

FIG. 8A depicts the implanting tool used to insert the implant 100 of FIG. 1A between vertebral bodies. FIG. 8A is a side view of the implantation tool 800 that has a handle 810 and an implant holder 820. The implant holder 820 has an implant conforming surface 824 and two pins 822 for holding a first plate 110 and a second plate 120 of a first half of the implant 100. The conforming surface 824 is curved to follow the convex outer edges 138, 139 of the plate 100, 120, respectively (shown in FIG. 3A). The implant 100 nests within a conforming surface 824 and is held by pins 822. FIG. 8C shows the distal view of the end of the tool with two pins 822, 823 for securing the first and second plate of the implant. The tool can be rotated by the user 180° to implant the other half of the implant.

Where an implant such as that shown in FIG. 6 is implanted, the implant conforming surface 824 of the implant tool would have a mirror image conforming surface provided to capture the implant 600. An additional series of pins, for a total of four, can be provided for holding a first plate 610 and a second plate 620 of the implant 600, if required. The implant 600 would nest within the conforming surface of the "U" shaped cavity.

A variety of kits can be assembled that include an implant 100 (or 600) sized for a particular patient. The kit could also include several cutting tools 700 and several implanting tools 800 or a single handle that cooperates with cutting ends 702 and implantation ends 820.

Figure 9:
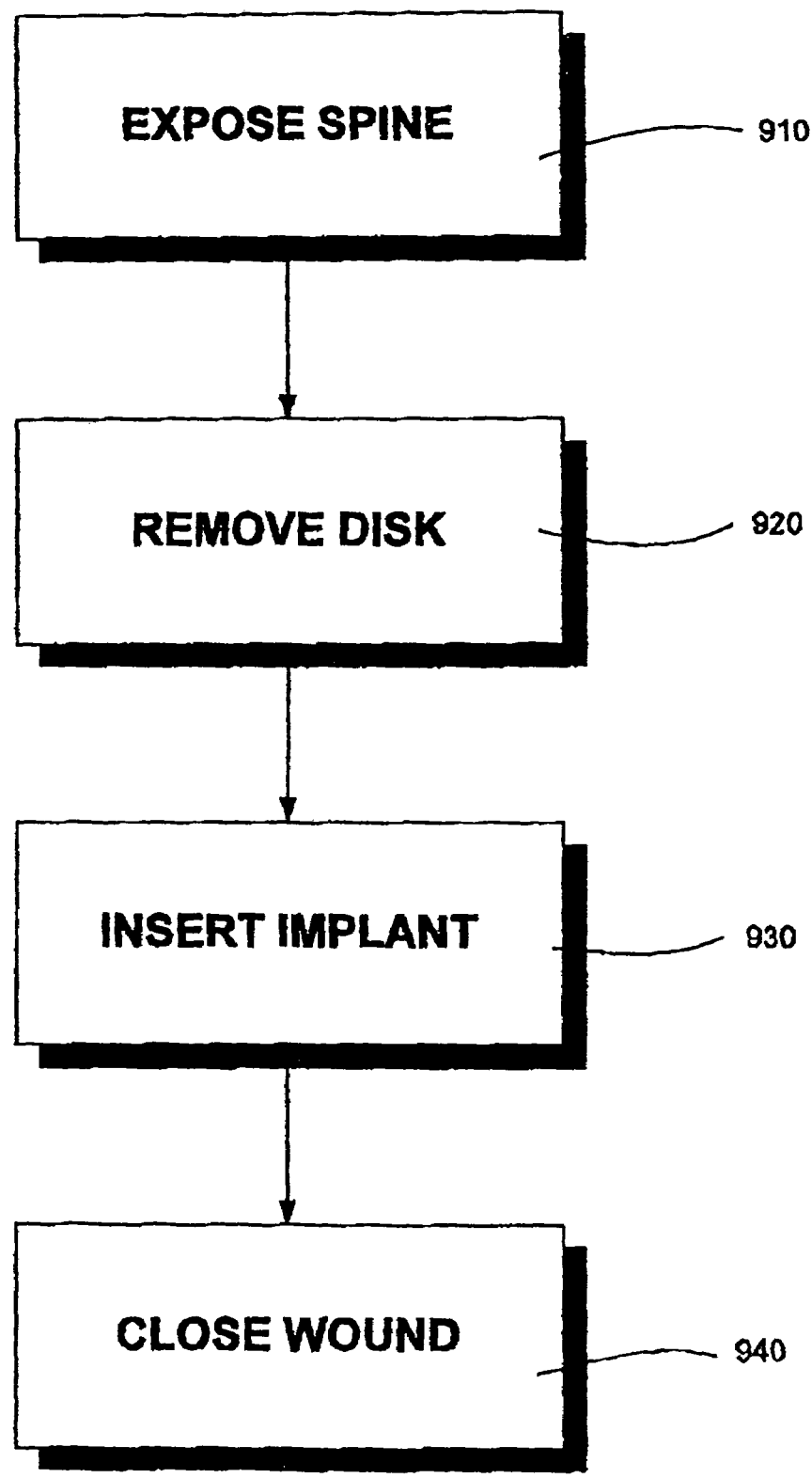
FIG. 9 is a block diagram illustrating the steps of a method for inserting the implant between vertebral bodies.

FIG. 9 is a block diagram showing the steps for implanting an implant. In order to implant the implant of FIG. 1A, the spine is exposed posteriorly 910. The intervertebral disk to be replaced is either partially or completely removed 920. The cutting tool 700 is inserted between the vertebral bodies to create channels in the bodies to receive the keels of the implant. Nerves can be retracted and then the implant holder 810 is used to insert the implant between the vertebral bodies 930, lining the keels up with the channels created by the cutting tool 700. Next, the nerves are retracted in the other direction and the other plates 100, 120 are attached to a tool and are implanted. The implant first and second plates 110, 120 are now inserted between the vertebrae, and the keel are placed in the channels prepared by the cutting tool 700. Once the implant is inserted, the wound is closed 940.

In order to implant the implant of FIG. 6, the spine is exposed anteriorly 910. The intervertebral disk to be replaced is either partially or completely removed 920. The cutting tool 700 is inserted between the vertebral bodies to create channels in the bodies to receive the keels of the implant. The implant is then inserted into an implant holder and the implant tool is used to insert the implant between the vertebral bodies 930, lining the keels up with the channels created by the cutting tool 700. Once the implant is inserted, the wound is closed 940.

The foregoing description of embodiments of the present invention has been provided for the purposes of illustration and description. It is not intended to be exhaustive or to limit the invention to the precise forms disclosed. Many modifications and variations will be apparent to the practitioner skilled in the art. The embodiments were chosen and described in order to best explain the principles of the invention and its practical application, thereby enabling others skilled in the art to understand the invention and the various embodiments and with various modifications that are suited to the particular use contemplated. It is intended that the scope of the invention be defined by the following claims and their equivalence.

What is claimed:

1. A tool for preparing vertebral bodies for an implant comprising: a cutter having, a forked end having a first tine and a second tine, said first and said second tines both having an upper surface and a lower surface, and both having an inner side and an outer side, wherein the inner side extends between the upper surface and the lower surface, and the outer side extends between the upper surface and the lower surface, a first cutting blade extending from the upper surface of said first tine and flush with the inner side of said first tine;

a second cutting blade extending from the upper surface of said second tine and flush with the inner side of said second tine and, said first and second cutting blades extending in a first direction from said first and said second tines; wherein the first and second cutting blades are adapted to cut a first pair of grooves in a first vertebral body in the first direction; and a third cutting blade extending from the lower surface of said first tine and flush with the outer side of said first tine; and a fourth cutting blade extending from the lower surface of said second tine and flush with the outer side of said second tine and, said third and fourth cutting blades extending in a second direction from said first and said second tines and said third and fourth cutting blades are placed further apart than the first and second cutting blades; wherein the third and fourth cutting blades are adapted to cut a second pair of grooves in a second vertebral body in the second direction; wherein the second direction is opposite from the first direction and the first and second pair of grooves are cut simultaneously in the first and second vertebral bodies, wherein the first, second, third, and fourth cutting blades each comprise a leading cutting edge extending substantially parallel to one of the inner and outer sides of the first or second tines.

2. The tool according to claim 1 wherein the tool is hand held; wherein the first and the second cutting blades are parallel to each other and over the entire length of the blade cutting surface, the first and second cutting blades are parallel to a handle of the tool, such that with the handle moving in a horizontal plane the first and second cutting blades will cut parallel grooves in the horizontal plane.

3. The tool according to claim 1 wherein the two tines have leading cutting edges that are beveled.

4. The tool according to claim 1 wherein the first and second cutting blades are coplanar with the inner side of each tine.

5. The tool according to claim 1 wherein the third and fourth cutting blades are coplanar with the outer side of each tine.

6. The tool according to claim 1 wherein the first, second, third and fourth cutting blades are positioned and adapted to bypass nerves.

7. The tool of claim 1 wherein the first and second tines have inboard and outboard beveled surfaces that converge and the first and second cutting blades have surfaces that are continuous with the inboard beveled surfaces and the third and fourth cutting blades have surfaces that are continuous with the outboard beveled surfaces.

8. The tool of claim 1 wherein the first and second cutting blades are upper cutting blades and the third and fourth cutting blades are lower cutting blades.

9. The tool of claim 1 wherein the third and fourth cutting blades are lower cutting blades positioned and adapted to bypass nerves.

10. A tool for preparing upper and lower vertebral bodies for an implant, the tool comprising:

(a) a cutter body having a thickness dimension between an upper surface and a lower surface to distract the upper and lower vertebral bodies apart a distance to receive an implant and having a side between the upper surface and lower surface facing a forward direction;

(b) a first pair of cutting blades protruding upwardly from the cutter body and adapted to cut a first pair of grooves in the upper vertebral body, wherein each blade of the first pair of blades is parallel to one another, and each blade of the first pair of blades includes a leading beveled cutting edge facing the forward direction and extending in the upward direction above the cutter body; and (c) a second pair of cutting blades protruding downwardly from the cutter body and adapted to cut a second pair of grooves in the lower vertebral body, wherein each blade of the second pair of blades is parallel to one another, and each blade of the second pair of blades includes a leading cutting edge extending in the downward direction below the cutter body, wherein the second pair of cutting blades are placed further apart than the first pair of cutting blades and wherein the first and second pair of cutting blades are parallel to one another, such that when the first pair of cutting blades cut first grooves through a first horizontal plane the second pair of cutting blades will cut second grooves through a second horizontal plane, wherein the first and second pair of grooves are parallel and are cut simultaneously in the upper and lower vertebral bodies; wherein the second pair of cutting blades are outboard of and spaced from the first pair of cutting blades.

11. A tool for preparing upper and lower vertebral bodies for an implant, the tool comprising:

a. a cutter body having a thickness dimension between an upper surface and a lower surface to distract the upper and lower vertebral bodies apart a distance to receive the implant and having a side between the upper surface and lower surface facing a forward direction;

b. a first pair of cutting blades protruding upwardly from the cutter body and adapted to cut a first pair of grooves in the upper vertebral body, each blade of the first pair of blades including a leading beveled cutting edge facing the forward direction and extending in the upward direction above the cutter body; and c. a second pair of cutting blades protruding downwardly from the cutter body and adapted to cut a second pair of grooves in the lower vertebral body, each blade of the second pair of blades including a leading cutting edge extending in the downward direction below the cutter body, wherein the second pair of cutting blades are placed further apart than the first pair of cutting blades and wherein the first and second pair of cutting blades are parallel to one another, such that when the first pair of cutting blades cut the first pair of grooves through a first horizontal plane through the upper vertebral body the second pair of cutting blades will cut parallel second pair of grooves through a second horizontal plane through the lower vertebral body, wherein the first and second pair of grooves are cut simultaneously in the upper and lower vertebral bodies; wherein the second pair of cutting blades are spaced from the first pair of cutting blades by the thickness dimension of the cutter body.

12. A tool with a handle by which it is held, for preparing upper and lower vertebral bodies for an implant, the tool comprising:

a. a cutter body having a thickness dimension between an upper surface and a lower surface to distract the upper and lower vertebral bodies apart a distance to receive the implant and having a side between the upper surface and lower surface facing a forward direction;

b. a first pair of cutting blades protruding upwardly from the cutter body and adapted to cut a first pair of grooves in the upper vertebral body, each blade of the firstpair of blades including a leading beveled cutting edge facing the forward direction and extending in the upward direction above the cutter body; and c. a second pair of cutting blades protruding downwardly from the cutter body and adapted to cut a second pair of grooves in the lower vertebral body, each blade of the second pair of blades including a leading cutting edge extending in the downward direction above the cutter body, wherein the second pair of cutting blades are placed further apart than the first pair of cutting blades and wherein the cutting blades of the first and second pairs of cutting blades are parallel to one another and wherein for the entire length of the blade cutting surface, the blades are parallel to the handle of the tool, such that with the handle moving in a horizontal plane the pair of first and second cutting blades will simultaneously cut parallel first and second grooves in the upper and lower vertebral bodies through respective horizontal planes.

* * * * *